United States Patent [19]
Dörreich et al.

[11] Patent Number: 5,474,922
[45] Date of Patent: Dec. 12, 1995

[54] β-1,4-GALACTANASE AND A DNA SEQUENCE

[75] Inventors: Kurt Dörreich, Grenzach-Wyhlen, Germany; Henrik Dalbøge, Virum; Jan M. Mikkelsen, Gentofte, both of Denmark; Marcel Mischler, Himmelried, Switzerland; Flemming M. Christensen, Rungsted Kyst, Denmark

[73] Assignee: Novo Nordisk A/S, Bagsvaerd, Denmark

[21] Appl. No.: 90,036

[22] PCT Filed: Feb. 6, 1992

[86] PCT No.: PCT/DK92/00037
    § 371 Date: Jul. 15, 1993
    § 102(e) Date: Jul. 15, 1993

[87] PCT Pub. No.: WO92/13945
    PCT Pub. Date: Aug. 20, 1992

[30] Foreign Application Priority Data

Feb. 6, 1991 [EP] European Pat. Off. ............. 91610007

[51] Int. Cl.⁶ .................. C12N 9/24; C12N 9/26; C12N 9/30; C12N 9/36
[52] U.S. Cl. ............. 435/200; 435/201; 435/203; 435/207; 435/208; 435/913; 424/94.61; 424/94.62
[58] Field of Search ............. 435/201, 203, 435/207, 208, 913, 917, 200; 424/94.61, 94.62

[56] References Cited

U.S. PATENT DOCUMENTS

| | | | |
|---|---|---|---|
| 4,478,854 | 10/1984 | Adler-Nissen et al. | 426/12 |
| 4,478,856 | 10/1984 | Adler-Nissen et al. | 426/46 |
| 4,483,874 | 11/1984 | Olsen | 426/44 |
| 4,891,096 | 1/1990 | Akkawi | 162/1 |

FOREIGN PATENT DOCUMENTS

| | | |
|---|---|---|
| 0221811 | 5/1987 | European Pat. Off. |
| 2302336 | 9/1976 | France. |
| 2518570 | 12/1982 | France. |
| 3529211 | 2/1987 | Germany. |
| 2115820 | 9/1983 | United Kingdom. |
| 2116977 | 10/1983 | United Kingdom. |

OTHER PUBLICATIONS

English Abstract of Jap. Pat. JP 2268685, Nov. 2, 1990.
English Abstract of Jap. Pat. JP 2308798, Dec. 21, 1990.
English Abstract of Jap. Pat. JP 3244382, Oct. 31, 1991.
English Abstract of Jap. Pat. JP 80-40238, Oct. 16, 1980.
English Abstract of Jap. Pat. JP 1296995, Nov. 30, 1989.
Abstract of Carbohydrate Res., vol. 190, No. 1, pp. 121–136 (1989).
Abstract of Abstr. Pap. Am. Chem. Soc. (195 Meet., BTEC27) (1988).
Abstract of Food Biotechnol., (4,1,553) 1990.
Nakano et al. (1991) CA 114:26275 Abstract of Kagaku to Kogyo 64(9), 440–445 (1990).

*Primary Examiner*—Keith C. Furman
*Attorney, Agent, or Firm*—Steve T. Zelson; Elias J. Lambiris

[57] ABSTRACT

The present invention relates to β-1,4-galactanase derived from *A. aculeatus* which have (a) a pH-optimum between 3.0 and 5.0, (b) an isoelectric point of 2.5–3.5, (c) a molecular weight of between 30,000 and 50,000, and (d) a temperature optimum between 10° and 50° C.

11 Claims, 13 Drawing Sheets

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 31 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
        ( A ) ORGANISM: Aspergillus aculeatus
        ( B ) STRAIN: CBS 101.43

( x i ) SEQUENCE DESCRIPTION: SEQ ID NO:1:

```
Ala  Leu  Thr  Tyr  Arg  Gly  Ala  Asp  Ile  Ser  Ser  Leu  Leu  Leu  Leu  Glu
 1                  5                        10                           15
Asp  Glu  Gly  Tyr  Ser  Tyr  Lys  Asn  Leu  Asn  Gly  Gln  Thr  Gln  Ala
                    20                       25                      30
```

( 2 ) INFORMATION FOR SEQ ID NO:2:

( i ) SEQUENCE CHARACTERISTICS:
        ( A ) LENGTH: 28 amino acids
        ( B ) TYPE: amino acid
        ( C ) STRANDEDNESS: single (D) TOPOLOGY: linear (ii) MOLECULE TYPE: peptide (iii) HYPOTHETICAL: NO (iv) ANTI-SENSE: NO (vi) ORIGINAL SOURCE:
 (A) ORGANISM: Aspergillus niger (xi) SEQUENCE DESCRIPTION: SEQ ID NO:2:

```
Ala Leu Thr Tyr Arg Gly Ala Asp Ile Ser Ser Leu Leu Ile Glu Glu
 1               5                  10                  15
Asp Ala Gly Ile Ser Tyr Lys Asn Leu Asn Gly Glu
            20                  25
```

(2) INFORMATION FOR SEQ ID NO:3:

(i) SEQUENCE CHARACTERISTICS:
  (A) LENGTH: 84 base pairs
  (B) TYPE: nucleic acid
  (C) STRANDEDNESS: single
  (D) TOPOLOGY: linear (ii) MOLECULE TYPE: rDNA (xi) SEQUENCE DESCRIPTION: SEQ ID NO:3:

GCGCTCACCT ATCGCGGCGC AGACATCTCT TCTCTCTTGC TGCTTGAAGA TGAGGGCTAT        60

AGCTATAAGA ATCTCAATGG CCAA        84

(2) INFORMATION FOR SEQ ID NO:4:

(i) SEQUENCE CHARACTERISTICS:
  (A) LENGTH: 72 base pairs
  (B) TYPE: nucleic acid
  (C) STRANDEDNESS: single
  (D) TOPOLOGY: linear (ii) MOLECULE TYPE: rDNA (xi) SEQUENCE DESCRIPTION: SEQ ID NO:4:

ACCCAAGCCC TAGAGACAAT TCTCGCCGAT GCTGGCATCA ATTCCATTCG TCAGCGTGTG        60

TGGGTGAACC CA        72

(2) INFORMATION FOR SEQ ID NO:5:

(i) SEQUENCE CHARACTERISTICS:
  (A) LENGTH: 60 base pairs
  (B) TYPE: nucleic acid
  (C) STRANDEDNESS: single
  (D) TOPOLOGY: linear (ii) MOLECULE TYPE: rDNA (xi) SEQUENCE DESCRIPTION: SEQ ID NO:5:

GCACGGCAGC TACATCTGGA CTACAATTTG GAGCTGGCCA AGGCGGTCAA GGCGCTGGCA        60

(2) INFORMATION FOR SEQ ID NO:6:

(i) SEQUENCE CHARACTERISTICS:
  (A) LENGTH: 39 base pairs
  (B) TYPE: nucleic acid
  (C) STRANDEDNESS: single
  (D) TOPOLOGY: linear (ii) MOLECULE TYPE: rDNA ( x i ) SEQUENCE DESCRIPTION: SEQ ID NO:6:

TCTGAATTGT GGGAGGGAGG GGATGAGTGC TCCGTCAGC                                    39

( 2 ) INFORMATION FOR SEQ ID NO:7:

( i ) SEQUENCE CHARACTERISTICS:
        ( A ) LENGTH: 67 base pairs
        ( B ) TYPE: nucleic acid
        ( C ) STRANDEDNESS: single
        ( D ) TOPOLOGY: linear ( i i ) MOLECULE TYPE: rDNA ( x i ) SEQUENCE DESCRIPTION: SEQ ID NO:7:

ACGTAACTAA CTAGAAGGTA GTTAGTTTAC TCCAAGTCTC CAAGCGACCA TTTTGCTACA             60

CACCGCC                                                                      67

( 2 ) INFORMATION FOR SEQ ID NO:8:

( i ) SEQUENCE CHARACTERISTICS:
        ( A ) LENGTH: 40 base pairs
        ( B ) TYPE: nucleic acid
        ( C ) STRANDEDNESS: single
        ( D ) TOPOLOGY: linear ( i i ) MOLECULE TYPE: rDNA ( x i ) SEQUENCE DESCRIPTION: SEQ ID NO:8:

GACGAGGGCC GGGGTATAAA CCAGGCCAGG GTCTCTAAAA                                   40

( 2 ) INFORMATION FOR SEQ ID NO:9:

( i ) SEQUENCE CHARACTERISTICS:
        ( A ) LENGTH: 96 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 16..96

( x i ) SEQUENCE DESCRIPTION: SEQ ID NO:9:

TAGCGAAGCT TCACA ATG CGT TCC TCC CCC CTC CTC CCG TCC GCC GTT GTG              51
               Met Arg Ser Ser Pro Leu Leu Pro Ser Ala Val Val
                1             5                10

GCC GCC CTG CCG GTG TTG GCC CTT GCA GCG CTC ACC TAT CGC GGC                   96
Ala Ala Leu Pro Val Leu Ala Leu Ala Ala Leu Thr Tyr Arg Gly
     15              20               25

( 2 ) INFORMATION FOR SEQ ID NO:10:

( i ) SEQUENCE CHARACTERISTICS:
        ( A ) LENGTH: 27 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

Met Arg Ser Ser Pro Leu Leu Pro Ser Ala Val Val Ala Ala Leu Pro
 1            5                10               15

Val Leu Ala Leu Ala Ala Leu Thr Tyr Arg Gly
        20              25

(2) INFORMATION FOR SEQ ID NO:11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

GGGCGTGAAT GTAAGCGTGA C        21

β-1,4-GALACTANASE AND A DNA SEQUENCE

CROSS-REFERENCE TO RELATED APPLICATIONS

This application is a continuation of PCT/DK92/00037 filed Feb. 6, 1992 which is incorporated herein be reference.

BACKGROUND OF THE INVENTION

1. Field of the Invention

The invention comprises a β-1,4-galactanase, a corresponding DNA sequence, a vector, a transformed host, a method for production of a β-1,4-galactanase, an enzyme preparation, and a use of the β-1,4-galactanase.

2. Description of Related Art

β-1,4-galactanases (EC no. 3.2.1.89) is a group of carbohydrases which degrade galactanes. The authorized enzyme name is 1,4-β-D-galactan galactohydrolase, but the short term β-1,4-galactanase is used in this specification with claims. Reference can be made to R. F. H. Dekker and G. N. Richards, "Hemicellulases, their Occurence, Purification, Properties and Mode of Action" in R. S. Tipson and D. Horton, Advances in Carbohydrate Chemistry and Biochemistry, Academic Press 32, 277–352 (1976), R. F. H. Dekker, "The Hemicellulase Group of Enzymes", in J. M. V. Blanchard and J. R. Mitchell, Polysaccharides in Food, Butterworths, 93–108 (1979), and A. G. J. Voragen, F. Geerst and W. Pilnik "Hemicellulases in Enzymatic Fruit Processing", in P. Depuy, Use of Enzymes in Food Technology, Technique et Documentation Lavoisier, 497–502 (1982). Galactanes are found in connection with many gums, agar, and fruit pectins, and they are components of cell walls in e.g. fruits and vegetables.

SUMMARY OF THE INVENTION

The present invention relates to β-1,14-galactanases obtainable from *A. aculeatus* which has a pH-optimum between 3.0 and 5.0, an isoelectric point of 2.5–3.5, a molecular weight of between 30,000 and 50,000, and temperature optimum between 10° and 50° C. The β1,4-galactanases may gave the partial amino acid sequence (SEQ ID NO: 1)

Ala Leu Thr Tyr Arg Gly Ala Asp Ile Ser Ser

Leu Leu Leu Leu Glu Asp Glu Gly Tyr Ser

Tyr Lys Asn Leu Asn Gly Gln Thr Gln Ala.

BRIEF DESCRIPTION OF THE DRAWINGS

The present invention is further illustrated by the drawings wherein.

Figure 1:
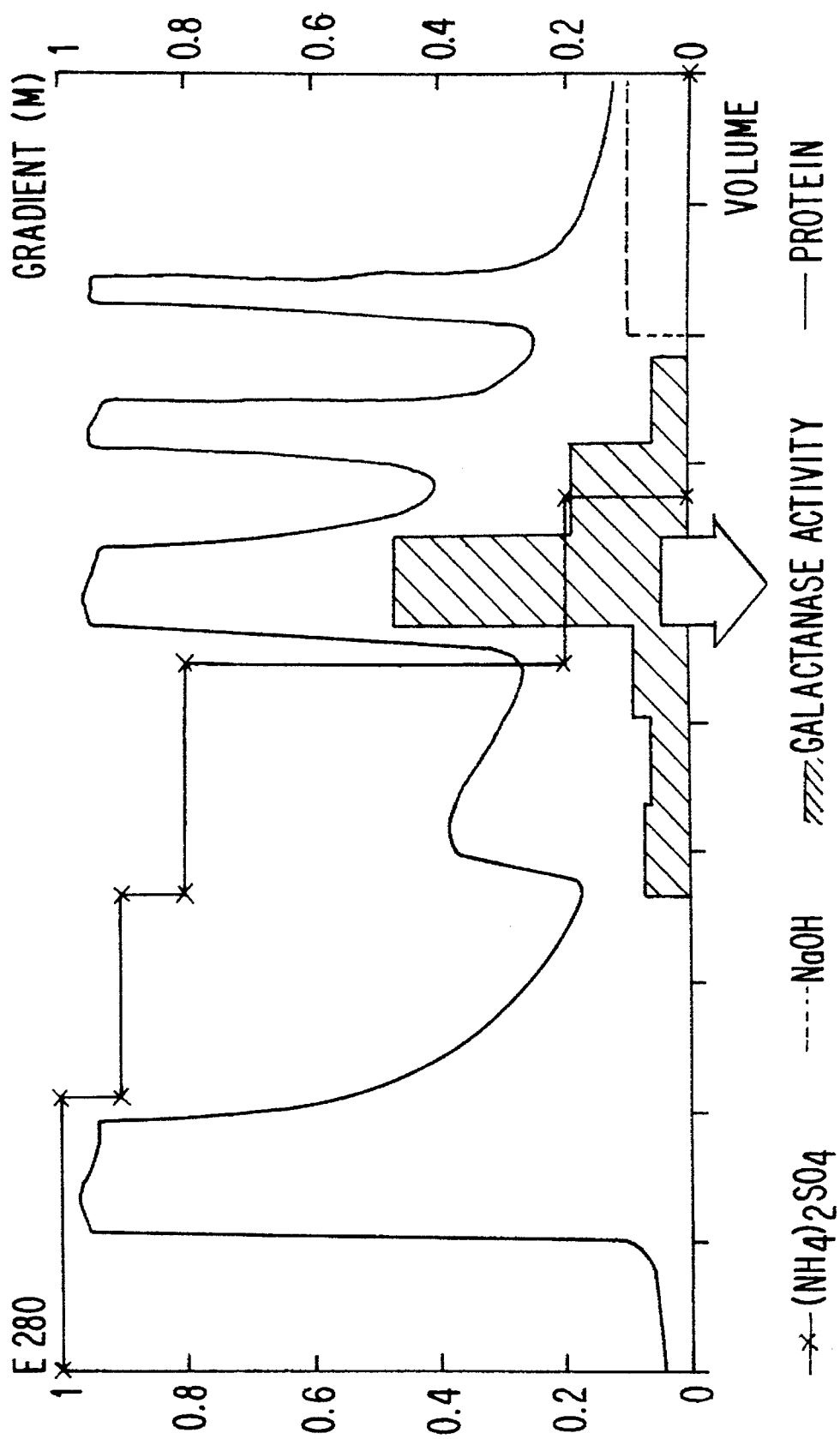
FIG. 1 graphically illustrates the results of hydrophobic interaction chromatography on a concentrated β-1,4-galactanase-containing broth from *Aspergillus aculeatus*.
Figure 2:
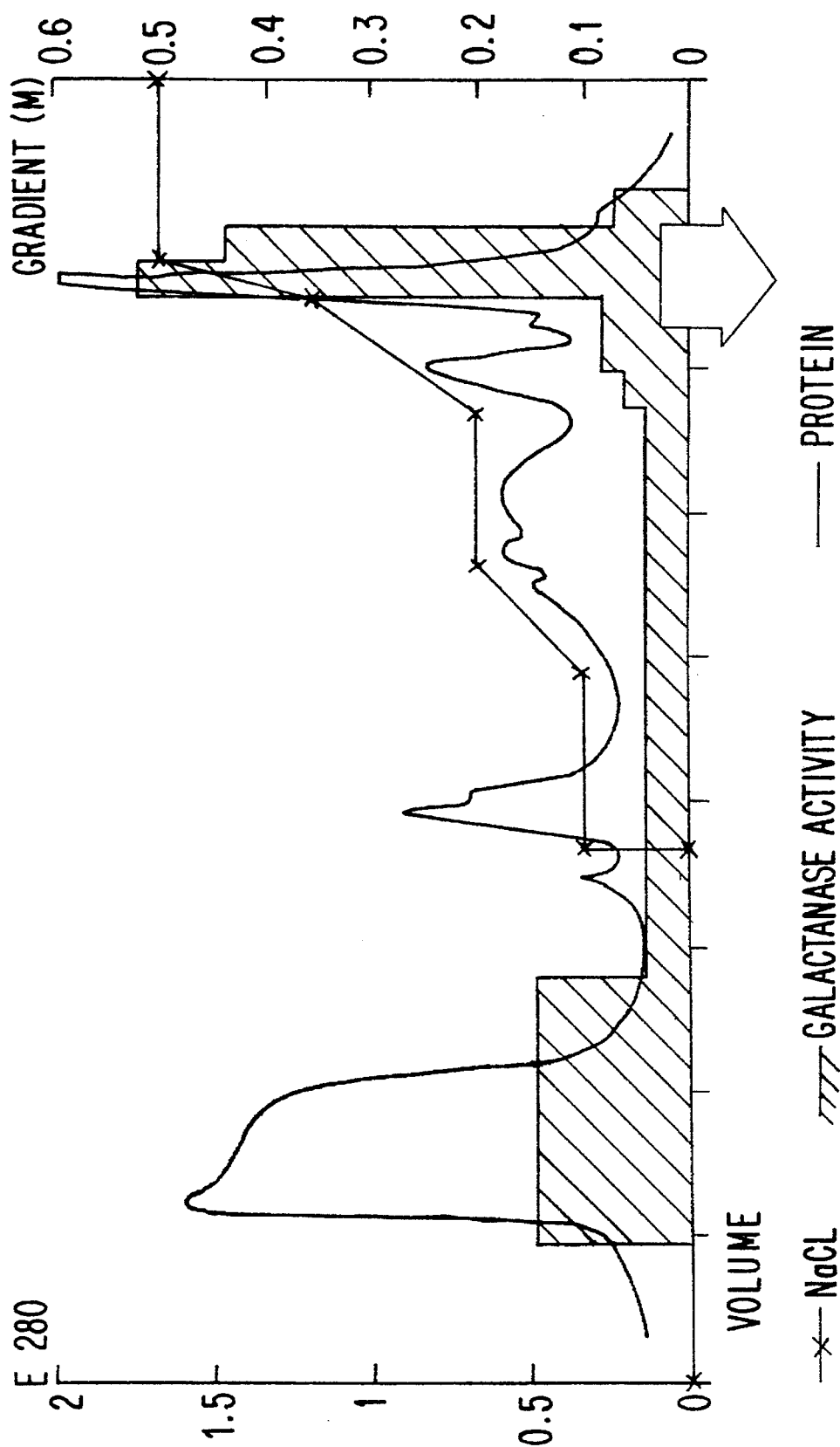
FIG. 2 graphically illustrates the results of ion exchange chromatography performed on the fraction of FIG. 1 which has been further diluted ultrafiltered.
Figure 3:
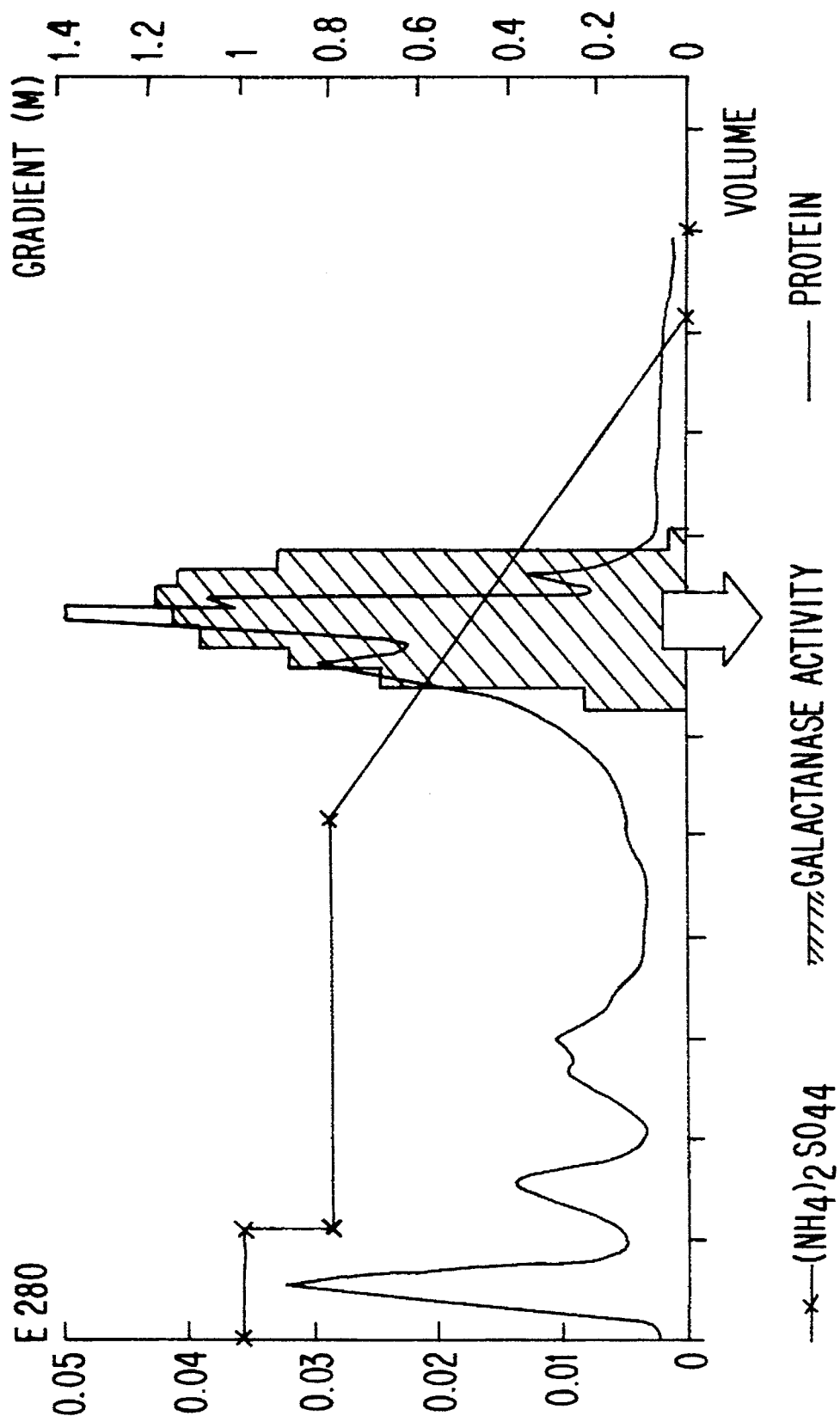
FIG. 3 graphically illustrates the results of pooled galactanase fractions treated by hydrophobic interaction chromatography.

The above indicated partial amino acid sequence can be used for construction of DNA probes which can be used for screening a genomic library for organisms expressing such enzyme, or a cDNA library, thereby obtaining DNA sequences, which can be used either for an overproduction of β-1,4-galactanase, if inserted in the microorganism species, from which the parent DNA molecule originated, or for production of β-1,4-galactanase without accompanying closely related enzymes, if inserted in a host microorganism, which in its not-transformed condition does not produce any enzymes closely related to β-1,4-galactanase. The DNA sequences can be established otherwise, as will appear from the following.

Thus, the purpose of the invention is the provision of a new β-1,4-galactanase and of means and methods for production of β-1,4-galactanase in better yield and higher purity than hitherto possible, and of a use of β-1,4-galactanase either alone or in combination with other enzymes for degradation of plant cell wall tissue, more efficient than hitherto possible. Also it is the purpose of the invention to provide novel products, wherein the proportion of the β-1, 4-galactanase is either increased or decreased in relation to the proportion in the original product.

The recombinant DNA sequence obtainable according to the invention comprises a DNA sequence coding for a polypeptide having β-1,4-galactanase activity, or a DNA sequence having substantial sequence homology to such β-1,4-galactanase coding sequence.

In the following it will be explained in detail how the recombinant DNA sequence according to the invention can be produced.

Crude enzyme preparations produced from *Aspergillus aculeatus* for purification of the β-1,4-galactanase can be produced as follows. For the sake of brevity this crude *Aspergillus aculeatus* preparation will be referred to in the following as A.a.e.p.

The strain *Aspergillus aculeatus* CBS 101.43 as a gene donor was fermented in a pilot plant scale in the following way.

An agar substrate with the following composition was prepared in a Fernbach flask:

| | |
|---|---|
| Peptone Difco | 6 g |
| Aminolin Ortana | 4 g |

-continued

| | |
|---|---|
| Glucose | 1 g |
| Yeast extract Difco | 3 g |
| Meat extract Difco | 1.5 g |
| KH$_2$PO$_4$ Merck | 20 g |
| Malt extract Evers | 20 g |
| Ion exchanged H$_2$O | ad 1000 ml | pH was adjusted to between 5.30 and 5.35. Then 40 g of Agar Difco was added, and the mixture was autoclaved for 20 minutes at 120° C. (the substrate is named E-agar).

The strain CBS 101.43 was cultivated on an E-agar slant (37° C.). The spores from the slant were suspended in sterilized skim-milk, and the suspension was lyophilized in vials. The contents of one lyophilized vial was transferred to the Fernbach flask. The flask was then incubated for 13 days at 30° C.

A substrate with the following composition was prepared in a 500 liter seed fermenter:

| | |
|---|---|
| CaCO$_3$ | 1.2 kg |
| Glucose | 7.2 kg |
| Rofec (corn steep liquor dry matter) | 3.6 kg |
| Soy bean oil | 1.2 kg |

Tap water was added to a total volume of around 240 liters. pH was adjusted to around 5.5 before addition of CaCO$_3$. The substrate was sterilized in the seed fermenter for 1 hour at 121° C. Final volume before inoculation was around 300 liters.

The Fernbach flask spore suspension was transferred to the seed fermenter. Seed fermentation conditions were:

Fermenter type: Conventional aerated and agitated fermenter with a height/diameter ratio of around 2.3.

| | |
|---|---|
| Agitation: | 300 rpm (two turbine impellers) |
| Aeration: | 300 normal liter air per minute |
| Temperature: | 30 to 31° C. |
| Time: | around 28 hours |

Around 28 hours after inoculation 150 liters was transferred from the seed fermenter to the main fermenter.

A substrate with the following composition was prepared in a 2500 liter main fermenter:

| | |
|---|---|
| Toasted soy meal | 90 kg |
| KH$_2$PO$_4$ | 20 kg |
| Pluronic ® antifoam agent | 150 ml |

Tap water was added to a total volume of around 900 liters. The toasted soy meal was suspended in water. pH was adjusted to 8.0 with NaOH, and the temperature was raised to 50° C. Thereafter around 925 Anson units of Alcalase® 0.6 L was added to the suspension. The mixture was held for 4 hours at 50° C. and pH= 8.0 (Na$_2$CO$_3$ addition) with no aeration and 100 rpm agitation. Thereafter the remaining substrate components were added and pH was adjusted to around 6.0 with phosphoric acid. The substrate was sterilized in the main fermenter for 1½ hours at 123° C. Final volume before inoculation was around 1080 liters.

Then 150 liters of seed culture was added.

Fermentation conditions were:

Fermenter type: Conventional aerated and agitated fermenter with a height/diameter ratio of around 2.7.

| | |
|---|---|
| Agitation: | 250 rpm (two turbine impellers) |
| Aeration: | 1200 normal liter air per minute |
| Temperature: | 30° C. |
| Time: | around 151 hours |

From 24 fermentation hours to around 116 fermentation hours pectin solution was added aseptically to the main fermenter at a constant rate of around 8 liters per hour. The pectin solution with the following composition was prepared in a 500 liter dosing tank:

| | |
|---|---|
| Pectin genu*) | 22 kg |
| Phosphoric acid, conc. | 6 kg |
| Pluronic ® antifoam agent | 50 ml |

*)Genu pectin (citrus type NF from the Copenhagen pectin factory Ltd.)

Tap water was added to a total volume of around 325 liters. The substrate was sterilized in the dosing tank for 1 hour at 121° C. Final volume before start of dosage was around 360 liters. When this portion ran out, another similar portion was made. Total volume of pectin solution for one fermentation was around 725 liters.

After around 151 fermentation hours the fermentation process was stopped. The around 1850 liters of culture broth were cooled to around 5° C. and the enzymes were recovered according to the following method.

The culture broth was drum filtered on a vacuum drum filter (Dorr Oliver), which was precoated with Hyflo Super-Cell diatomaceous earth (filter aid). The filtrate was concentrated by evaporation to around 15% of the volume of the culture broth. The concentrate was filtered on a Seitz filter sheet (type supra 100) with 0.25% Hyflo Super-Cell as a filter aid (in the following table referred to as filtration I). The filtrate was precipitated with 561 g of (NH$_4$)$_2$SO$_4$/l at a pH of 5.5, and 4% Hyflo Super-Cell diatomaceous earth is added as a filter aid. The precipitate and the filter aid are separated by filtration on a frame filter. The filter cake is dissolved in water, and insoluble parts are separated by filtration on a frame filter. The filtrate is check filtered on a Seitz filter sheet (type supra 100) with 0.25% Hyflo Super-Cell as a filter aid (in the following table referred to as filtration II). The filtrate is diafiltered on an ultrafiltration apparatus. After diafiltration the liquid is concentrated to a dry matter content of 12.7% (in the following table referred to as dry matter content in concentrate).

A facultative base treatment for partial removal of the protease activity can be carried out at this stage. In case the base treatment is used it is carried out at a pH of 9.2 for 1 hours, whereafter the pH value is adjusted to 5.0.

Now the liquid is check filtered and filtered for the purpose of germ reduction and the filtrate is freeze-dried on a freeze-drying equipment from Stokes.

The pure β-1,4-galactanase is obtainable from the A.a.e.p. as shown in Table 1.

TABLE 1

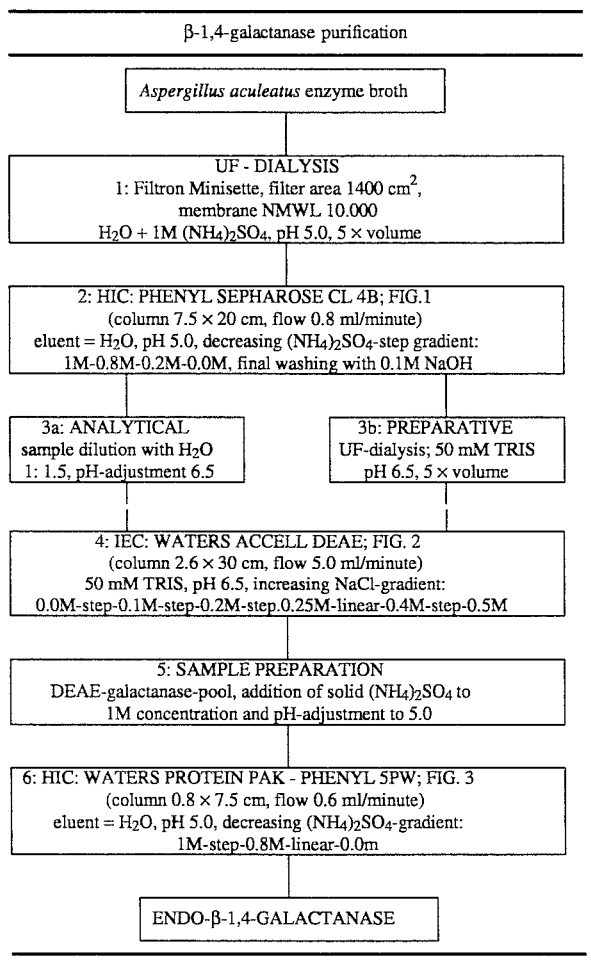

ad 1:
Concentration and buffer exchange in order to prepare for step 2, removal of small particles and about 50% of the colour ad 2:
HIC is hydrophobic interaction chromatography. The colorless β-1,4-galactanase fraction is pooled from step 0.8–0.2M $(NH_4)_2SO_4$.

ad 3:
a—Dilution in order to reduce the salt concentration in the sample
b—Buffer exchange in order to prepare for step 4 ad 4:
IEC is ion exchange chromatography. The β-1,4-galactanase fraction is pooled from step 0.25–0.5M NaCl ad 5:
Buffer adaption in order to prepare for step 6.

ad 6:
The active galactanase fraction was pooled in the range of 0.4M $(NH_4)_2SO_4$. This fraction shows with IEF (isoelectric focusing) one band. On SDS-PAGE (sodium dodecyl sulfate polyacrylamide gel electrophoresis)/silver 3 protein bands were detected, where the main fraction amounts to more than 80% of the protein in the test. The same pictures appeared with/without DTT (dithio threitol). Immuno-blotting by means of an antibody raised against the A.a.e.p. generated the same picture as SDS-PAGE/silver.

All efforts to separate these 3 bands on HPLC failed. Further investigations on the N-terminals indicated that the sample is a pure enzyme fraction, and that the accompanying bands are artefacts originating from the sample preparation and working conditions.

The below indicated Table 2 shows how the enrichment factor increases as the purification proceeds.

TABLE 2

| Step | Procedure | Protein (mg) | Enzyme activity (U-units) | Specific activity (U/mg) | Enzyme yield (%) | Enrichment factor |
|---|---|---|---|---|---|---|
| Initial | crude enzyme | 2.842 | 539.000 | 190 | 100 | 1.0 |
| 2 | Phenyl Sepharose CL4B | 847 | 440.000 | 519 | 82 | 2.7 |
| 4 | Accell DEAE | 31 | 330.000 | 10.645 | 61 | 56.1 |
| 6 | Protein PAK Phenyl 5PW | 8 | 250.000 | 31.250 | 46 | 164.8 |

Unit definition

The U unit indicated in Table 2 is the β-1,4-galactanase activity unit, which is defined as follows: 1 unit is the amount of enzyme which at 30° C. and in 1 minute releases 1 μmole of galactose from potato galactan, as described later.

Amino acid sequence

The following partial amino acid sequence was determined from the purified β-1,4-galactanase by means of automated sequencing (Applied Biosystems 473A protein sequencer)

```
 1               5                  10                                          (SEQ ID NO: 1)
Ala—Leu—Thr—Tyr—Arg—Gly—Ala—Asp—Ile—Ser—Ser—Leu—Leu—Leu—

15              20                 25
Leu—Glu—Asp—Glu—Gly—Tyr—Ser—Tyr—Lys—Asn—Leu—Asn—Gly—Gln—

30
Thr—Gln—Ala—
```

Thus, the β-1,4-galactanase according to the invention is characterized by the fact that it exhibits the following partial amino acid sequence Isoelectric point: pH 2.8

```
 1               5                  10                                          (SEQ ID NO: 1)
Ala—Leu—Thr—Tyr—Arg—Gly—Ala—Asp—Ile—Ser—Ser—Leu—Leu—Leu—

15              20                 25
Leu—Glu—Asp—Glu—Gly—Tyr—Ser—Tyr—Lys—Asn—Leu—Asn—Gly—Gln—

30
Thr—Gln—Ala—
``` or a partial amino acid sequence with a homology thereto of at least 70%, preferably at least 80%, more preferably at least 90%. Ala no. 1 in the partial sequence is assumed to be the N-terminal amino acid.

On the basis of the sequences the purity of the sample is estimated to be more than 90%.

The amino acid sequences of the β-1,4-galactanase show no homology with other proteins in the UW-GCG data bank, a publicly available data bank, in relation to which UW is an abbreviation for University of Wisconsin.

The β-1,4-galactanase is further characterized, as indicated in the following.

Figure 4:
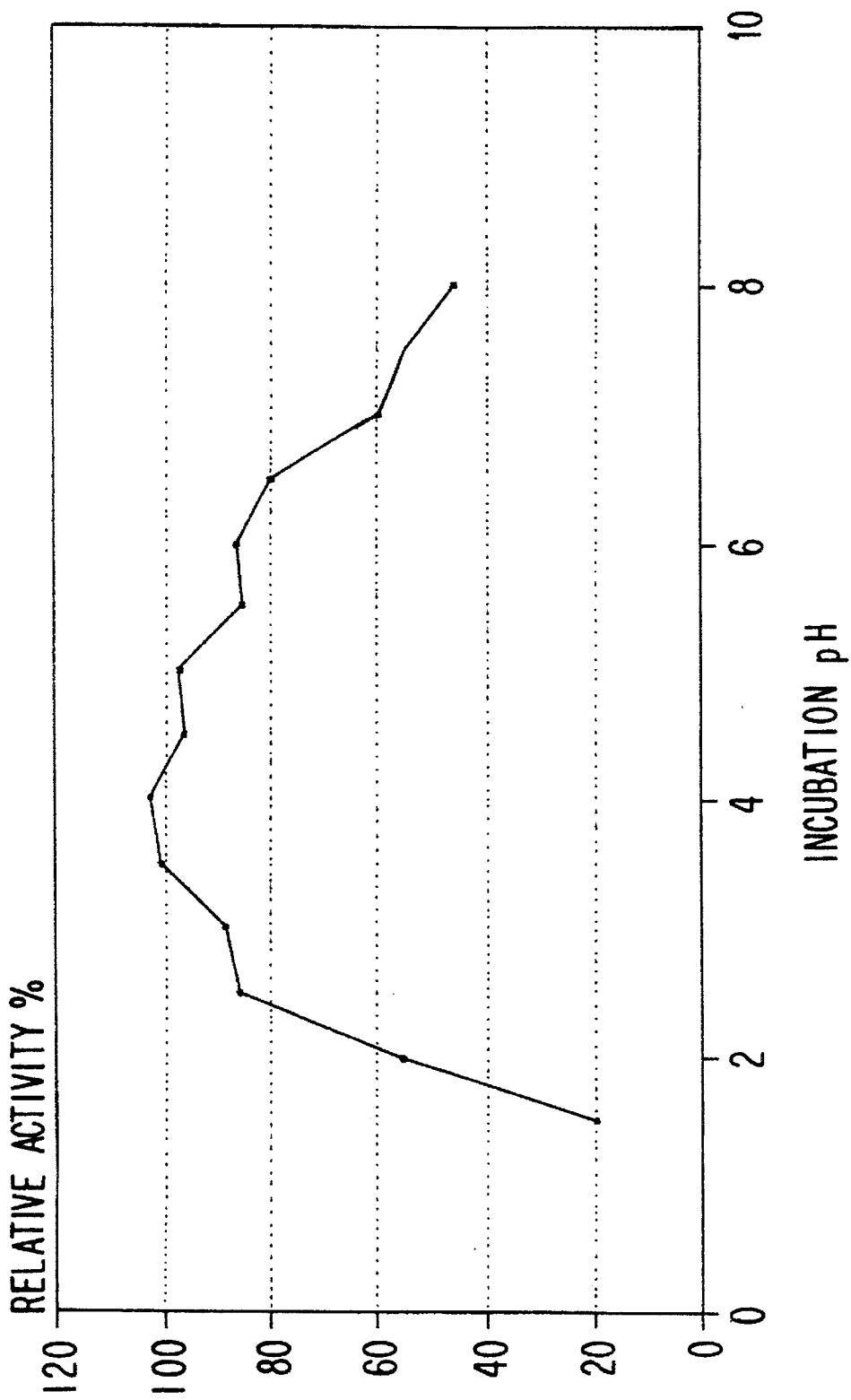
FIG. 4 graphically illustrates the activity of β-1,4-galactanase of the invention as a function of pH.
Figure 5:
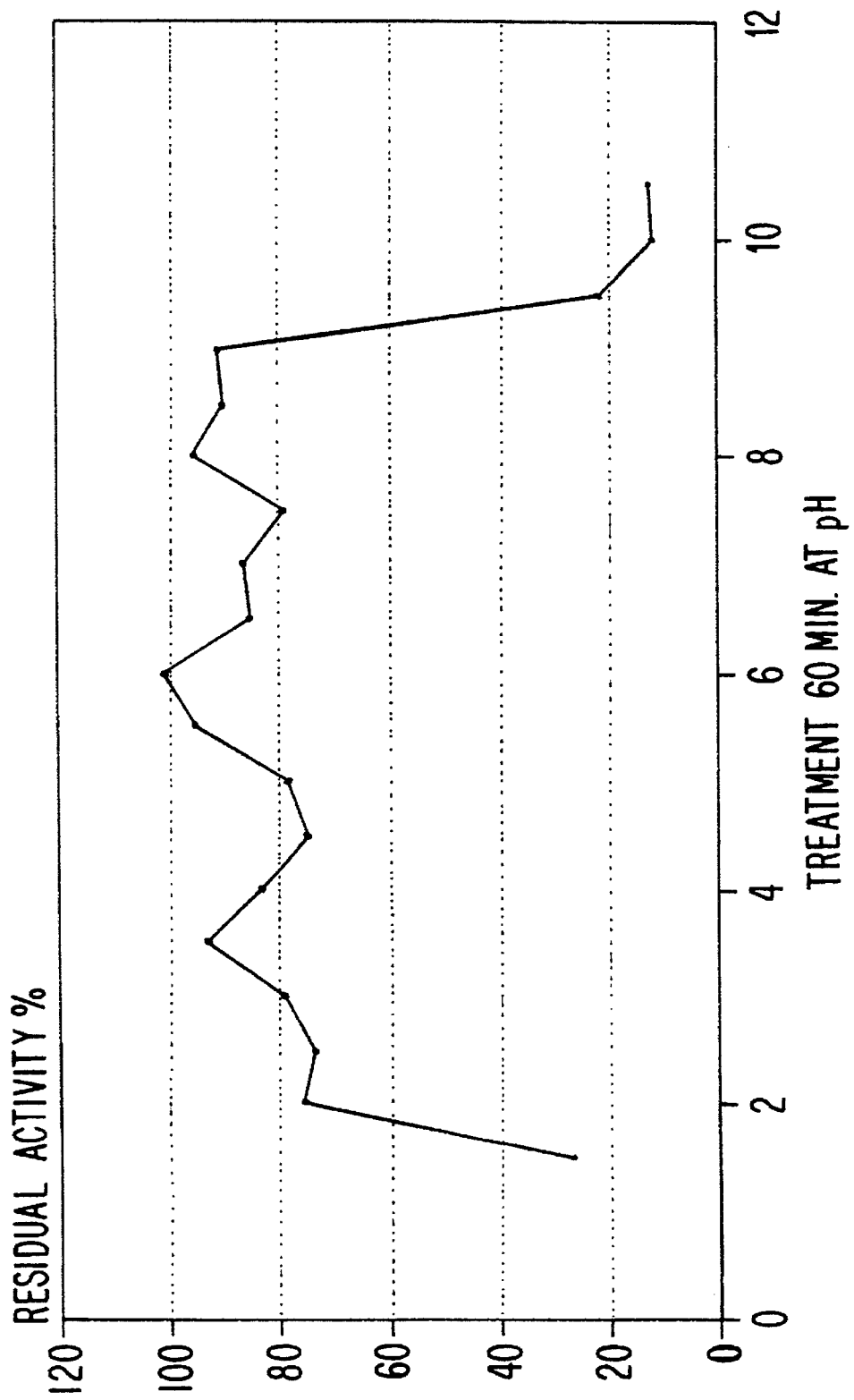
FIG. 5 graphically illustrates the stability of a β-1,4-galactanase of the invention as a function of pH.

FIGS. 4 and 5 show the pH activity and pH stability, respectively, of the β-1,4-galactanase.

This β-1,4-galactanase shows a relatively broad pH-spectrum with pH-optimum at pH 3.5–4.0.

The β-1,4-galactanase is relatively acid stable. The stability is good between pH 2 and 8, when treated for 1 hour at room temperature.

Figure 6:
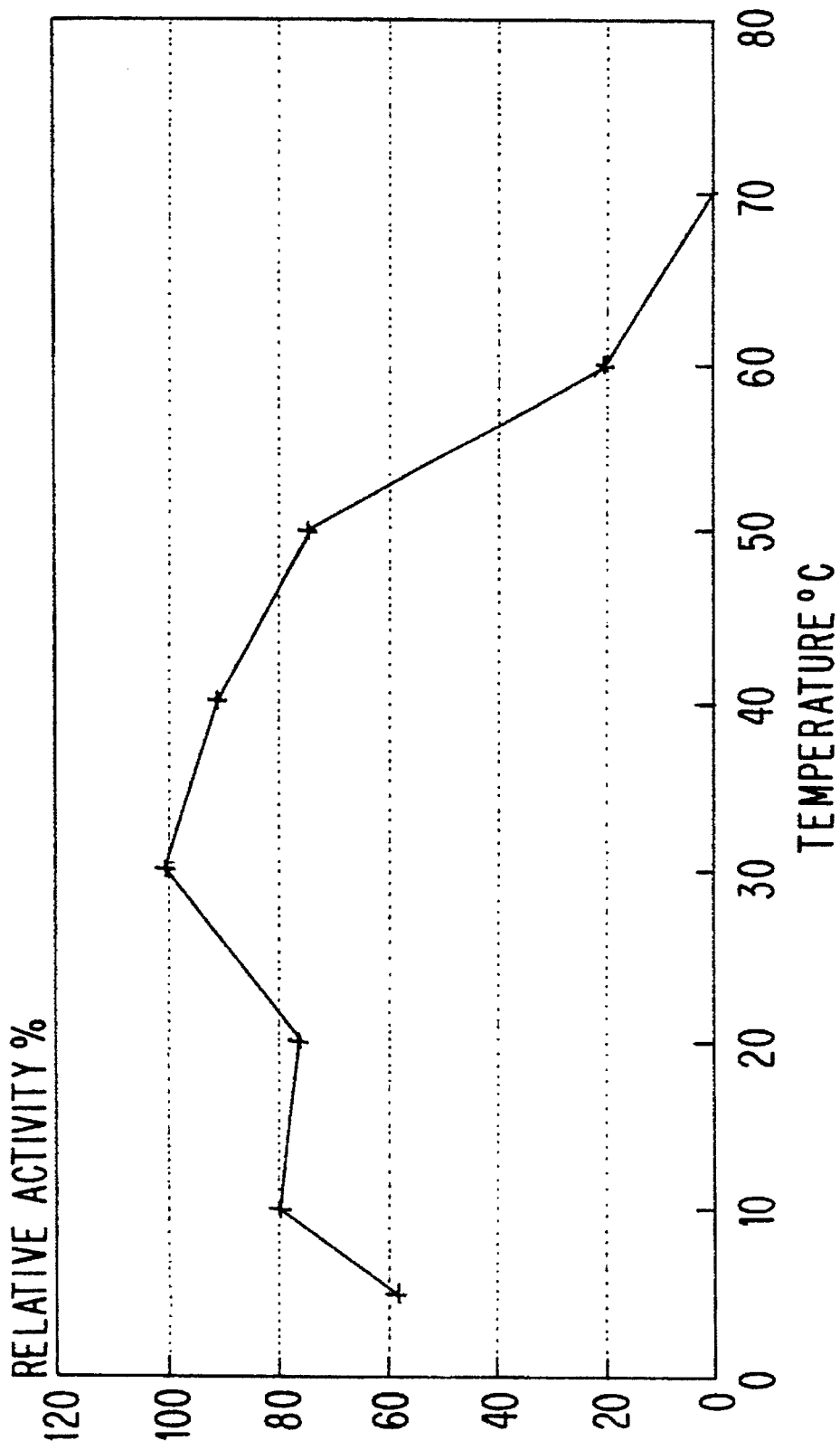
FIG. 6 graphically illustrates the activity of a β-1,4-galactanase of the invention as a function temperature.
Figure 7:
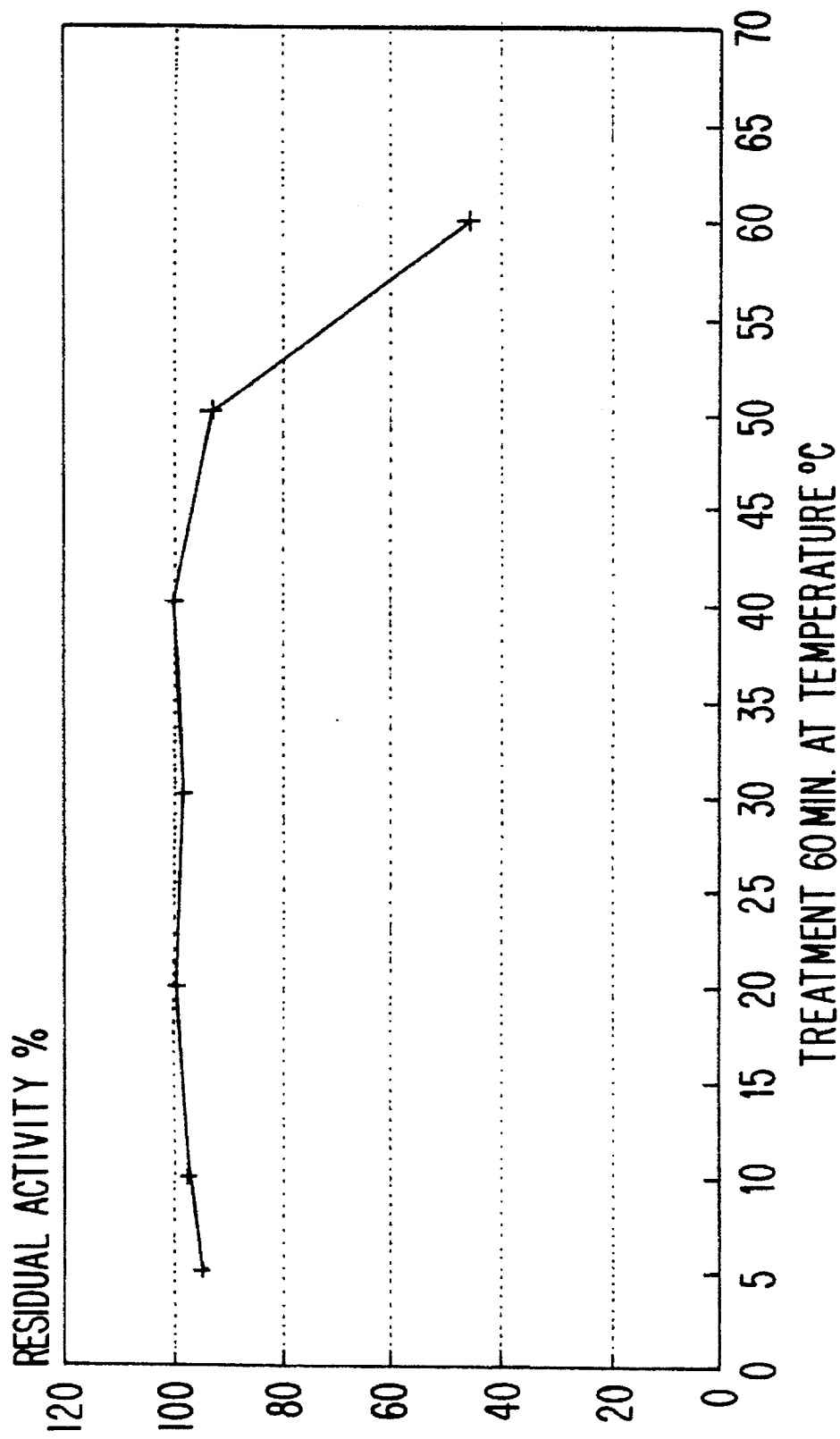
FIG. 7 graphically illustrates the stability of a β-1,4-galactanase of the invention as a function temperature.

FIGS. 6 and 7 show the temperature activity dependency and the temperature stability dependency, respectively, of the β-1,4-galactanase.

The temperature optimum of the β-1,4-galactanase is around 30° C., and the temperature activity range is relatively broad. For the fruit juice and wine area the activity in the low temperature range is very remarkable:

around 60% activity at 5° C.

around 80% activity at 10° C.

In the temperature range of 5°–55° C. the β-1,4-galactanase activity is not remarkably influenced after a treatment of 1 hour at pH 4.5 (≧80% of the initial activity).

Molecular weight: 40.000 Dalton

Figure 8:
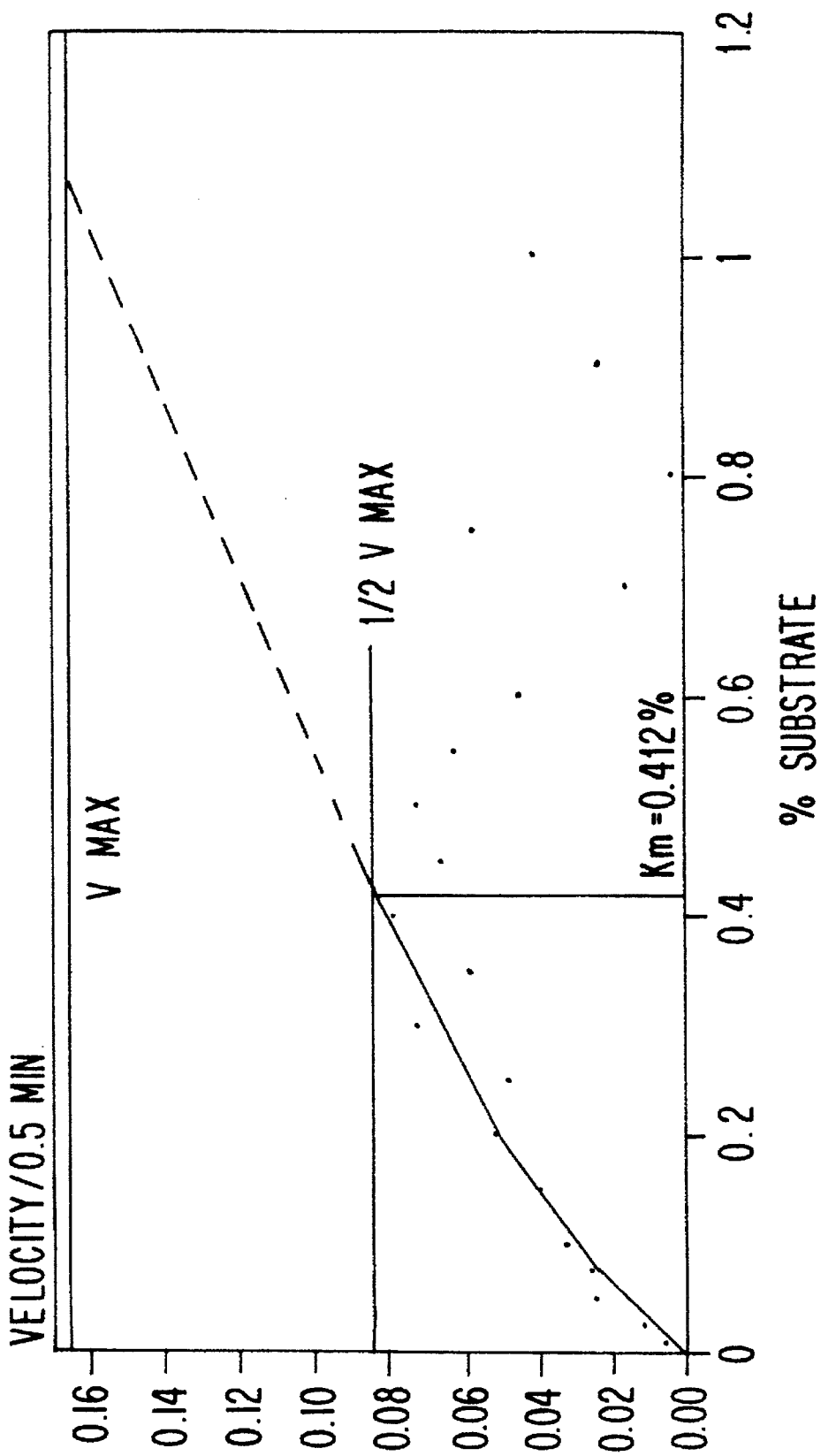
FIG. 8 graphically illustrates the determination of Michaelis-Menten-Kinetic of a β-1,4-galactanase of the invention.
Figure 9:
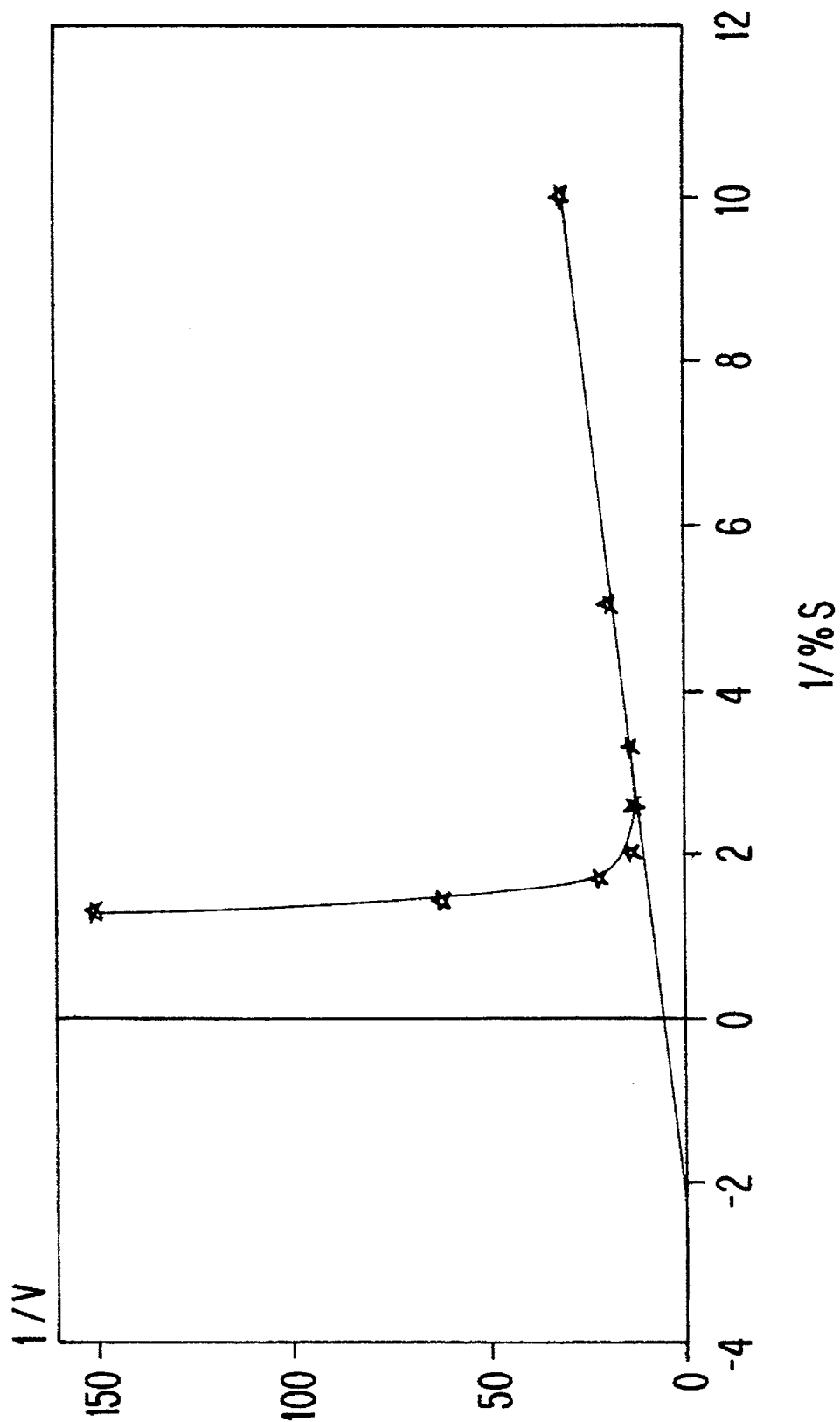
FIG. 9 graphically illustrates the determination of the Lineweaver-Burk-kinetic or a β-1,4-galactanase of the invention.

Km-value: The Michaelis-Menten-Kinetic and the corresponding Lineweaver-Burk-kinetic appears from FIGS. 8 and 9, respectively. The resulting Km-value is expressed in %-substrate concentration (not in mole/l, the reason for this being the inhomogenity of the molecular weight distribution of the substrate; therefore it was not possible to calculate an accurate figure for the molecular weight).

The β-1,4-galactanase is inhibited by substrate concentrations ≧0.3%. The theoretical and calculated Km-value is Km=0.41% NNFAG-potato-galactan From a pectinase preparation (Pectinex® AR) produced by means of a strain of Aspergillus niger another β-1,4-galactanase was isolated, and a partial amino acid sequence was determined:

```
 1               5                  10              15                          (SEQ ID NO: 2)
Ala—Leu—Thr—Tyr—Arg—Gly—Ala—Asp—Ile—Ser—Ser—Leu—Leu—Ile—Glu—

20                 25
Glu—Asp—Ala—Gly—Ile—Ser—Tyr—Lys—Asn—Leu—Asn—Gly—Glu—
```

Due to the fact that this partial amino acid sequence exhibits a homology to the amino acid sequene indicated in claim 1 of more than 70% the β-1,4-galactanase originating from the Aspergillus niger strain is within the scope of the invention. Also, the fact that this β-1,4-galactanase has been found useful as a plant cell wall degrading agent in combination with the fact that the homology thereof with the β-1,4-galactanase characterized in claim 1 is more than 70% justifies the scope of claim 1 in regard to the fact that the homology is more than 70%.

A preferred embodiment of the β-1,4-galactanase according to the invention is characterized by the fact that the β-1,4-galactanase exhibits a pH-optimum of 3.0–5.0, an isoelectric point of 2.0–3.5, a molecular weight of between 30,000 and 50,000, and a temperature optimum between 10° and 50° C.

A preferred embodiment of the β-1,4-galactanase according to the invention is characterized by the fact that the β-1,4-galactanase exhibits a pH-optimum of 3.5–4.0, an isoelectric point of 2.5–3.1, a molecular weight of between 37,000 and 45,000, and a temperature optimum between 25° and 40° C.

Also the invention comprises a recombinant DNA sequence, which is characterized by encoding for the β-1,4-galactanase according to the invention.

A preferred embodiment of the recombinant DNA sequence according to the invention is characterized by the fact that it comprises at least one of the following partial DNA sequences A preferred embodiment of the vector according to the invention is characterized by the fact that the vector is pHD438.

Also the invention comprises a transformed host which is characterized by the fact that it contains the vector according to the invention.

A preferred embodiment of the transformed host according to the invention is characterized by the fact that the transformed host is an Aspergillus strain. Hereby a good production capacity of the β-1,4-galactanase is obtained.

A preferred embodiment of the transformed host according to the invention is characterized by the fact that the transformed host is a strain belonging to the species *Aspergillus aculeatus, Aspergillus niger, Aspergillus oryzae* or *Aspergillus awamori*. Hereby a good production capacity of the β-1,4-galactanase is obtained.

A preferred embodiment of the transformed host according to the invention is characterized by the fact that the transformed host is a microorganism, which in its non-transformed condition does not produce β-1,4-galactanase or only produces β-1,4-galactanase in insignificant amounts.

| | | |
|---|---|---|
| 1) | GCG CTC ACC TAT CGC GGC GCA GAC ATC TCT TCT CTC TTG CTG CTT GAA GAT GAG GGC TAT AGC TAT AAG AAT CTC AAT GGC CAA | (SEQ ID NO: 3) |
| 2) | ACC CAA GCC CTA GAG ACA ATT CTC GCC GAT GCT GGC ATC AAT TCC ATT CGT CAG CGT GTG TGG GTG AAC CCA | (SEQ ID NO: 4) |
| 3) | GCA CGG CAG CTA CAT CTG GAC TAC AAT TTG GAG CTG GCC AAG GCG GTC AAG GCG CTG GCA | (SEQ ID NO: 5) |
| 4) | TCT GAA TTG TGG GAG GGA GGG GAT GAG TGC TCC GTC AGC | (SEQ ID NO: 6) |
| 5) | ACG TAA CTA ACT AGA AGG TAG TTA GTT TAC TCC AAG TCT CCA AGC GAC CAT TTT GCT ACA CAC CGC C | (SEQ ID NO: 7) |
| 6) | GA CGA GGG CCG GGG TAT AAA CCA GGC CAG GGT CTC TAA AA | (SEQ ID NO: 8) |

A preferred embodiment of the recombinant DNA sequence according to the invention is characterized lay the fact that it comprises a DNA sequence selected from a) the *Aspergillus aculeatus* β-1,4-galactanase DNA insert pHD 438 b) a DNA sequence which hybridizes to the coding region for the mature β-1,4-galactanase DNA comprised by the DNA insert of a) and which comprises a structural gene for a polypeptide with β-1,4-galactanase activity, and optionally a promoter, a coding region for a signal or leader peptide and/or transcriptional terminator.

c) a DNA sequence with a homology sufficient to hybridize to one of the sequences indicated in claim 3 under relative stringent conditions (1.0× SSC, 0.1% SDS, 65° C.), reference being made to T. Maniatis et al., Molecular cloning, A laboratory Manual, Cold Spring Harbor, 1982, or d) a DNA sequence which codes for a mature β-1,4-galactanase or a signal peptide or a leader peptide thereof and which is degenerate within the meaning of the genetic code with respect to a DNA sequence of a), b) or c).

Also, the invention comprises a vector which is characterized by the fact that it comprises the recombinant DNA sequence according to the invention.

A preferred embodiment of the vector according to the invention is characterized by the fact that the promoter is the *Aspergillus oryzae* takaamylase promoter. This vector is deposited at DSM on Feb. 3, 1992 (deposit no. DSM 6901).

Hereby a "tailor made" enzyme preparation with high β-1,4-galactanase activity and a spectrum of other wanted specific enzyme activities can be obtained.

A preferred embodiment of the transformed host according to the invention is characterized by the fact that the transformed host is *Bacillus sp., E. coli* or *S. cerevisiae*.

Also, the invention comprises a method for production of a β-1,4-galactanase by use of a transformed host according to the invention. By means of this method the β-1,4-galactanase can be obtained in high yield.

Also, the invention comprises the β-1,4-galactanase, when produced by the method according to the invention. The β-1,4-galactanase can be obtained in high yield.

Also, the invention comprises an enzyme preparation which is characterized by the fact that it contains a pectinase preparation usable for degradation or modification of plant cell walls enriched with the β-1,4-galactanase according to the invention. In this manner a boosting of the cell wall degrading ability of the pectinase preparation can be obtained.

Also, the invention comprises an enzyme preparation which is characterized by the fact that it contains a pectinase preparation usable for degradation or modification of plant cell walls enriched with the β-1,4-galactanase according to the invention with an enrichment factor of at least 1.1.

A preferred embodiment of the enzyme preparation according to the invention is characterized by the fact that the pectinase preparation is producible by means of a microorganism belonging to the genus Aspergillus. Such preparation is able to provide an extraordinary good total liquefaction power and thus a marked viscosity decrease of apple mash and similar biological materials. This will be documented in a later part of the specification in case the pectinase preparation is A.a.e.p.

A preferred embodiment of the enzyme preparation according to the invention is characterized by the fact that the pectinase preparation is producible by means of *Aspergillus niger, Aspergillus aculeatus, Aspergillus awamori* or *Aspergillus oryzae*.

A preferred embodiment of the enzyme preparation according to the invention is characterized by the fact that the β-1,4-galactanase is the β-1,4-galactanase produced by means of the method according to the invention. The production costs of this preparation are relatively low.

Also, the invention comprises a use of the β-1,4-galactanase according to the invention as an agent for degradation or modification of galactanes.

A preferred embodiment of the use of the β-1,4-galactanase according to the invention is a use as an agent for degradation or modification of plant cell walls. At present, degradation of plant cell walls is the most preferred use of the β-1,4-galactanase according to the invention, due to the high plant cell wall degradation activity.

Also the invention comprises a use of the enzyme preparation according to the invention as an agent for degradation or modification of galactanes.

A preferred embodiment of the use of the enzyme preparation according to the invention is a use as an agent for degradation or modification of plant cell walls. At present, degradation of plant cell walls is the most preferred use of the enzyme preparation according to the invention, due to the high plant cell wall degradation activity.

Figure 10:
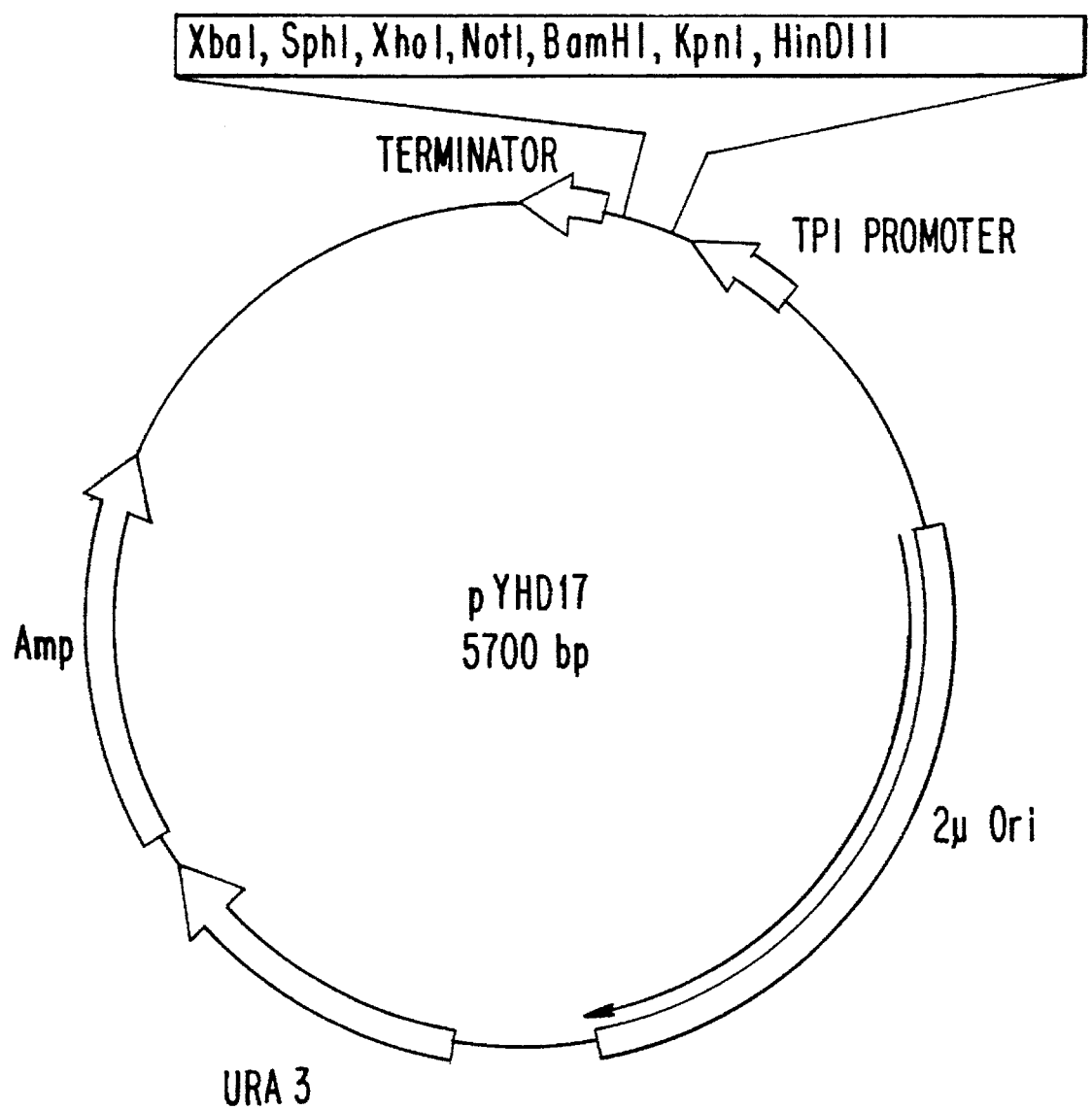
FIG. 10 shows a map of plasmid pYHD17.

FIG. 10 is a map of plasmid pYHD17, wherein "TPI promoter" indicates the *S. cerevisiae* triose phosphate isomerase promoter, "Terminator" indicates the transcription terminator, "Amp" indicates the gene mediating ampicillin resistance, "2 μori" indicates the yeast plasmid 2 μ origin of replication, and "URA3" indicates a gene encoding a selection marker complementing a uracil deficiency in the host strain.

Construction of an expression plasmid

The commercially available plasmid pYES II (Invitrogen) was cut with SpeI, filled in with Klenow DNA polymerase+ dNTP and cut with ClaI. The DNA was size fractionated on an agarose gel, and a fragment of about 2000 bp was purified by electroelution. The same plasmid was cut with ClaI/ PvuII, and a fragment of about 3400 bp was purified by electroelution. The two fragments were ligated to a blunt-ended SphI/EcoRI fragment containing the yeast TPI promoter. This fragment was isolated from a plasmid in which the TPI promoter from *S. cerevisiae* (cf. T. Albers and G. Kawasaki, *J. Mol. Appl. Genet.* 1, 1982, pp. 419–434) was slightly modified: an internal SphI site was removed by deleting the four bp constituting the core of this site. Furthermore, redundant sequences upstream of the promoter were removed by Ball exonuclease treatment followed by addition of a SphI linker. Finally, an EcoRI linker was added at position −10. After these modifications, the promoter is included in a SphI-EcoRI fragment. Its effeciency compared to the original promoter appears to be unaffected by the modifications. The resulting plasmid pYHD17 is shown in FIG. 10.

Donor organism mRNA was isolated from *Aspergillus aculeatus* CBS 101.43 grown in a soya-rich fermentation medium with agitation to ensure sufficient aeration.

Isolation of mRNA

Total RNA was isolated from approximately 7 g of mycelium. The mycelium was frozen in liquid nitrogen and ground in a mortar with 1 g of quartz sand to a consistency of flour. The RNA was extracted with guanidinium thiocyanate and centrifuged through CsCl essentially as described in Sambrook et al., 1989, op. cit. Poly A RNA was isolated from total RNA by chromatrography on oligo dT cellulose.

cDNA synthesis cDNA synthesis was carried out by means of a cDNA synthesis kit from Invitrogen according to the manufacturer's specifications. The DNA was adapted to the expression vectors by addition of a BstxI linker (Invitrogen) and size fractionated on an agarose gel. Only DNA larger than 5–600 bp was used in the library construction. The adapted cDNA was ligated into an appropriate vector cut with BstxI. Following test ligations (in order to determine the size of the library) the library was plated onto 50 agar plates. To each plate containing from approximately 500 to 5000 individual clones (dependent on the library size) was added 3 ml medium. The bacteria were scraped off, 1 ml glycerol was added, and stored at −80° C. as 50 pools. The remaining 2 ml were used for DNA isolation. If the amount of DNA was insufficient to give the required number of yeast transformants (see below), large scale DNA was prepared from 500 ml medium (TB) inoculated with 50 μl −80° C. bacterial stock propagated over night.

Construction of Yeast Libraries

DNA from one or more pools was transformed into yeast as described below. To ensure that all the bacterial clones were tested in yeast a number of yeast transformants 5×larger than the number of bacteria clones in the original pools was set as a limit.

Transformation of yeast

The yeast strain used was yNG231. (MAT alpha, leu2, ura3-52, his4-539, pep4-delta 1, cir+). One colony was grown at 30° C. overnight in 10 ml YPD (this culture can be stored for several days at 5° C.).

10, 30, and 60 μl of this culture were added to 3 shaker flasks containing 100 ml YPD, and incubated with shaking overnight at 30° C. The culture with an $OD_{500}$ closest to 0.3–0.4 was selected. The cells were harvested in 50 ml tubes in a Beckman centrifuge (speed 6, 10 minutes), the cells were resuspended in 2×5 ml $H_2O$, centrifuged as described above, resuspended in 5 ml buffer containing 0.1M LiAc, 10 mM Triso-Cl, 1 mM EDTA, pH 7.5, and centrifuged again. The cells were resuspended in 500 μl of the above buffer and incubated for 60 minutes at 30° C. 250 μl g carrier DNA (sterile salmon-sperm DNA 10 mg/ml) was added and aliquots of 100 μl were prepared. The DNA to be transformed (approx. 5 μg) was added to the 100 μl aliquot, mixed gently, and incubated for 30 minutes at 30° C. 700 μl 40% PEG 4000, 0.1M LiAc, 10 mM Tris-Cl, 1 mM EDTA, pH 7.5 was added, and incubation was continued for 60 minutes at 30° C. The transformation mixture was subjected to heat shock for 5 minutes at 42° C., spun briefly in a micro centrifuge, resuspended in 100–200 μl $H_2O$, and plated on SC plates without uracil, followed by incubation for three days at 30° C.

Preparation of carrier DNA 100 mg salmon-sperm DNA was weighed out and dissolved overnight in 10 ml 10 mM Tris-Cl, 1 mM EDTA, pH 7,5 (TE). The solution was then sonicated in a plastic container in ice water until it was no longer viscous. The solution was then phenole extracted and EtOH precipitated, and the pellet was washed and resuspended in 5 ml TE. The suspension was EtOH precipitated, and the pellet was washed and resuspend in 5 ml TE. The $OD_{260}$ was measured, and the suspension was diluted with TE to 10 mg/ml.

Transformation of *Aspergillus oryzae* or *Aspergillus niger* (general procedure)

100 ml of YPD (Sherman et al., Methods in Yeast Genetics, Cold Spring Harbor Laboratory, 1981) is inoculated with spores of *A. oryzae* or *A. niger* and incubated with shaking at 37° C. for about 2 days. The mycelium is harvested by filtration through miracloth and washed with 200 ml of 0.6M $MgSO_4$. The mycelium is suspended in 15 ml of 1.2M $MgSO_4$. 10 mM $NaH_2PO_4$, pH=5.8. The suspension is cooled on ice and 1 ml of buffer containing 120 mg of Novozym® 234, batch 1687 is added. After 5 minutes 1 ml of 12 mg/ml BSA (Sigma type H25) is added and incubation with gentle agitation continued for 1.5–2.5 hours at 37° C. until a large number of protoplasts is visible in a sample inspected under the microscope.

The suspension is filtered through miracloth, the filtrate transferred to a sterile tube and overlayered with 5 ml of 0.6M sorbitol, 100 mM Tris-HCl, pH=7.0. Centrifugation is performed for 15 minutes at 100 g and the protoplasts are collected from the top of the $MgSO_4$ cushion. 2 volumes of STC (1.2M sorbitol, 10 mM Tris-HCl, pH=7.5. 10 mM $CaCl_2$) are added to the protoplast suspension and the mixture is centrifugated for 5 minutes at 1000 g. The protoplast pellet is resuspended in 3 ml of STC and repelleted. This is repeated. Finally the protoplasts are resuspended in 0.2–1 ml of STC.

100 μl of protoplast suspension is mixed with 5–25 μg of the appropriate DNA in 10 μl of STC. Protoplasts are mixed with p3SR2 (an *A. nidulans* amdS gene carrying plasmid). The mixture is left at room temperature for 25 minutes. 0.2 ml of 60% PEG 4000 (BDH 29576). 10 mM $CaCl_2$ and 10 mM Tris-HCl, pH=7.5 is added and carefully mixed (twice) and finally 0.85 ml of the same solution is added and carefully mixed. The mixture is left at room temperature for 25 minutes, spun at 2500 g for 15 minutes and the pellet is resuspended in 2 ml of 1.2M sorbitol. After one more sedimentation the protoplasts are spread on the appropriate plates. Protoplasts are spread on minimal plates (Cove Biochem.Biophys.Acta 113 (1966) 51–56) containing 1.0M sucrose, pH=7.0, 10 mM acetamide as nitrogen source and 20 mM CsCl to inhibit background growth. After incubation for 4–7 days at 37° C. spores are picked and spread for single colonies. This procedure is repeated and spores of a single colony after the second reisolation is stored as a defined transformant.

Construction of an Aspergillus expression vector

Figure 11:
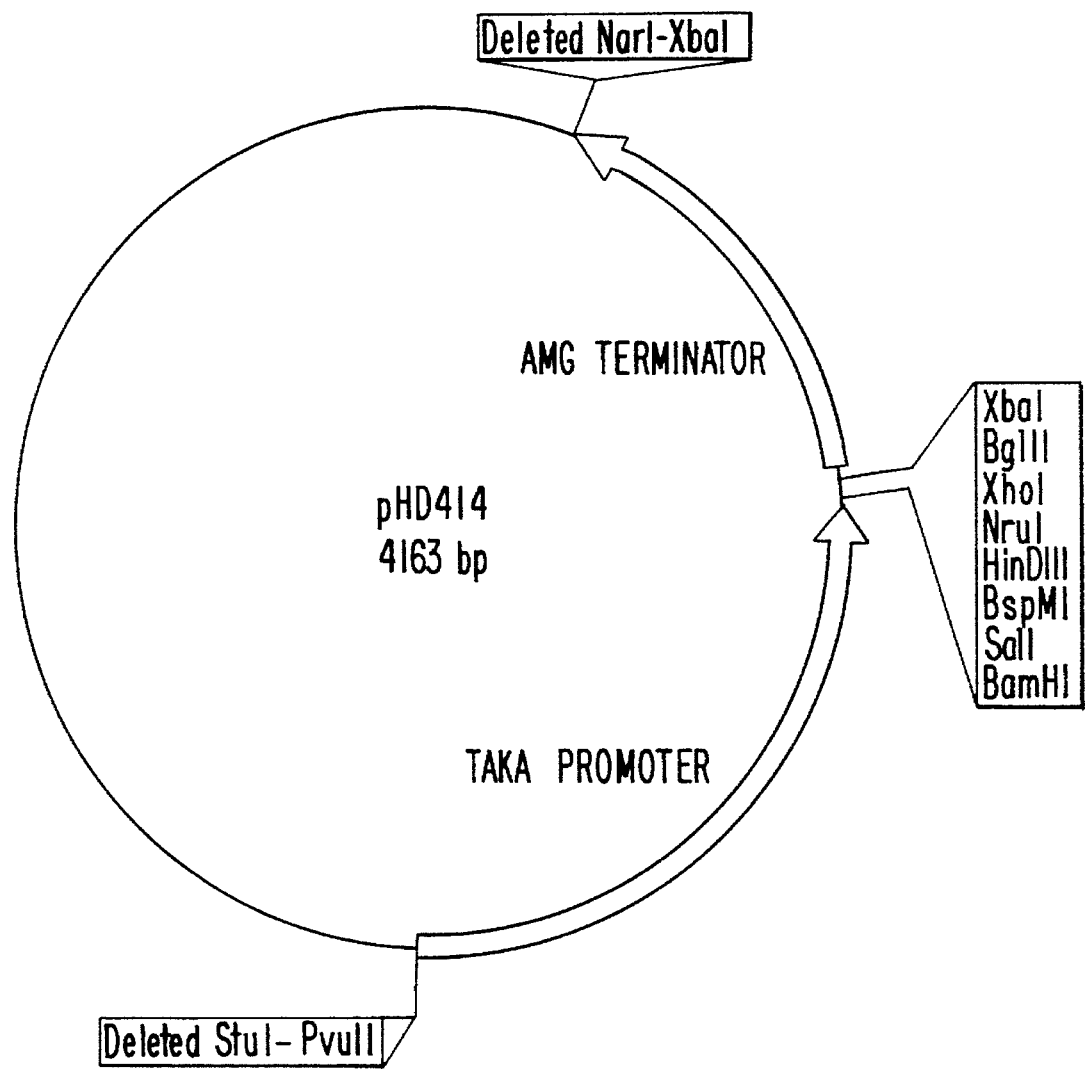
FIG. 11 shows a map of plasmid pHD414.

The vector pHD414 (FIG. 11) is a derivative of the plasmid p775 (described in EP 238 023). In contrast to this plasmid, pHD 414 has a string of unique restriction sites between the promoter and the terminator. The plasmid was constructed by removal of an approximately 200 bp long fragment (containing undesirable RE sites) at the 3'end of the terminator, and subsequent removal of an approximately 250 bp long fragment at the 5'end of the promoter, also containing undesirable sites. The 200 bp region was removed by cleavage with NarI (positioned in the pUC vector) and XbaI (just 3' to the terminator), subsequent filling in the generated ends with Klenow DNA polymerase+ dNTP, purification of the vector fragment on gel and religation of the vector fragment. This plasmid was called pHD413. pHD413 was cut with StuI (positioned in the 5'end of the promoter) and PvuII (in the pUC vector), fractionated on gel and religated, resulting in pHD414. FIG. 11 is a map of plasmid pHD414, wherein "AMG Terminator" indicates the *A. niger* glucoamylase terminator, and "TAKA Promoter" indicates the *A. oryzae* TAKA amylase promoter.

Production of potato galactan

β-1,4-galactan can be obtained from potato fibres by means of the following procedure:

Fresh waste material from a starch factory is used as a starting material (very low starch content, dry matter substance (DMS) around 17%).

Prior to extraction of galactan, the residual soluble starch has to be removed by an α-amylase treatment (Termamyl® 120 L). The potato fibres are diluted with water (1 part of fibres: 3 parts of water), the pH adjusted to pH 6.5 with NaOH, and the mixture is heated to 65° C. The α-amylase (0.2% Termamyl® 120 L based on DMS) is added and the residual starch is broken down with a treatment time of less than 2 hours.

Afterwards the extraction of the galactan is performed in accordance with the general procedure of Labavitch et al. (1976) for galactan from citrus pectin, with few adjustments (Labavitch, J. M., L. E. Freeman, P. Albersheim, Structure of Plant Cell Walls. Purification and characterization of a β-1,4-galactanase which degrades a structural component of the primary cell walls of dicots, J. Biol. Chem., 251, 5904–5910 (1976)). The pH of the starch free material is adjusted to pH 11.4, and subsequently the mixture is heated to 90° C. and stirred for 20 hours (pH control). After cooling to room temperature, the material is neutralised to pH 614 7 (with $H_3PO_4$), centrifuged, filtered and ultrafiltered.

The thus produced arabinogalactan (MW around 40,000 Daltons) is then treated with 0.05M trifluoro acetic acid at 100° C. for 1 hour in order to remove the arabinose side chains from the galactan. The reaction is stopped by cooling the solution and evaporating the trifluoro acetic acid. Finally the solution is diafiltered to a sugar free state and freeze dried.

The resulting β-1,4-galactan exhibits a molecular weight around 13,000 Daltons.

Production of soy galactan

Arabino galactan is produced with soy remanence as a starting material. In principle the same method is used as the method published by Labavitch et al. in J.Biol.Chem. 251, p. 5904–5910 (1976).

Media

YPD: 10 g yeast extract, 20 g peptone, $H_2O$ to 810 ml. Autoclaved, 90 ml 20% glucose (sterile filtered) added.

YPG-agar: 25 g/L Bactoagar, 15 g/L glucose, 5 g/L $K_2PO_4$, 0.5 g/L $MgSO_4$-$7H_2O$, pH adjusted to 5.0. Autoclaved.

10×Basal salt: 66.8 g yeast nitrogen base, 100 g succinic acid, 60 g NaOH, $H_2O$ ad 1000 ml, sterile filtered.

SC-URA: 90 ml 10×Basal salt, 22.5 ml 20% casamino acids, 9 ml 1% tryptophane, $H_2O$ ad 806 ml, autoclaved, 3.6 ml 5% threonine and 90 ml 20% glucose added.

SC-H agar: 7.5 g/l yeast nitrogen base without amino acids, 11.3 g/l succinic acid, 6.8 g/l NaOH, 5.6 g/l casamino acids without vitamins, 0.1 g/l tryptophan and 20 g/l agar (Bacto). Autoclaved for 20 min. at 121° C. After autoclaving, 55 ml of a 22% galactose solution and 1.8 ml of a 5% threonine solution were added per 450 ml agar.

YNB-1 agar: 3.3 g/l $KH_2PO_4$, 16.7 g/g agar, pH adjusted to 7. Autoclaved for 20 min. at 121° C. After autoclaving, 25 ml of a 13.6% yeast nitrogen base without amino acids, 25 ml of a 40% glucose solution, 1.5 ml of a 1% L-leucine solution and 1.5 ml of a 1% histidine solution were added per 450 ml agar.

YNB-1 broth: Composition as YNB-1 agar, but without the agar.

Soy galactan overlayer gel: 1% agarose, 0, 1% galactan in 0, 1M citrate-phosphate buffer, pH 4.5. The gel was boiled and then cooled to 55° C. before the overlayer was poured onto agar plates.

FG-4-Agar: 35 g/L agar, 30 g/L Soy bean meal, 15 g/L maltodextrin (Glucidex 6), 5 g/L Bacto pepton, pH 7. Autoclaved 40 min at 121° C.

FG-4 medium: 30 g/L Soy bean meal, 15 g/L maltodextrin (Glucidex 6), 5 g/L Bacto pepton. Autoclaved 40 min at 121° C.

MDU-2 medium: 45 g/L maltose, 1 g/L $MgSO_4$-7 $H_2O$, 1 g/L NaCl, 2 g/L $K_2SO_4$, 12 g/L $KH_2PO_4$, 0.1 ml/L Pluronic 61 L, 0.5 ml/L Trace metal solution. pH 5.0. Autoclaved 20 min at 121° C. 15 ml/L 50% steril filteret urea is added after autoclavation.

Trace metal solution: 13.9 g/L $FeSO_4$-7$H_2O$, 8.45 g/L $MnSO_4$-$H_2O$, 6.8 g/L $ZnCl_2$, 2.5 g/L $CuSO_4$-5$H_2O$, 0.24 g/L $NiCl_2$-6$H_2O$, 3 g/L citric acid.

EXAMPLE 1

A library from *Aspergillus aculeatus* CBS 101.43 consisting of approx. 300,000 individual clones in 50 pools was constructed in *E. coli* as previously described.

DNA was isolated from 20 individual clones from the library and subjected to analysis for cDNA insertion. The insertion frequency was found to be >90% and the average insert size was approximately 1400 bp.

DNA from the *Aspergillus aculeatus* library, was transformed into yeast, and plates containing 20–30,000 colonies were obtained from each pool. The colonies were scraped off and stored in glycerol at −80° C.

Yeast cells from the library were spread onto YNB agar to a total of about 250,000 colonies. The number of colonies per plate varied from 50 to 500. After 4 or 5 days of growth, the agar plates were replica plated onto two sets of SC-H agar plates. These plates were then incubated for 2–4 days at 30° C. before the two sets of agar plates were overlayered with a β-1,4-galactan overlayer gel for detection of galactanase activity, the β-1,4-galactan being produced as indicated above. After incubation overnight at 40° C., enzyme reactions were visualised with Congo Red. First 10–15 ml 0,5M tris-borate buffer pH 8.4 was poured onto the plates and removed after approx. 30 min. The 10–15 ml of a 0.1% solution of Congo Red was poured onto the overlayer and removed after 10–20 min. The plates were then washed once or twice by pouring 10–15 ml of 2M NaCl onto the plates. The NaCl solution was removed after 15–25 min. Galactanase-positive colonies were identified as colonies with colourless or pale red clearing zones on a red background.

Cells from enzyme-positive colonies were spread for single colony isolation on agar, and an enzyme-producing single colony was identified and selected by the above described galactan overlayer method.

A galactanase positive yeast isolate was identifitied and confirmed positive.

EXAMPLE 2

Isolation of DNA

The isolate was inoculated into 20 ml YNB-1 broth in a 50 ml glass test tube. The tube was shaken for 2 days at 30° C. The cells were harvested by centrifugation for 10 min. at 3000 rpm.

The cells were resuspended in 1 ml 0.9M sorbitol, 0.1M EDTA, pH 7.5. The pellet was transferred to an Eppendorf tube, and spun for 30 seconds at full speed. The cells were resuspended in 0.4 ml 0.9M sorbitol, 0.1M EDTA, 14 mM β-mercaptoethanol. 100 μ2 mg/ml Zymolase was added, and the suspension was incubated at 37° C. for 30 minutes and spun for 30 seconds. The pellet (spheroplasts) was resuspended in 0.4 ml TE. 90 μl of (1.5 ml 0.5M EDTA pH 8.0, 0.6 ml 2M Tris-Cl pH 8.0, 0.6 ml 10% SDS) was added, and the suspension was incubated at 65° C. for 30 minutes. 80 μl 5M KOAc was added, and the suspension was incubated on ice for at least 60 minutes and spun for 15 minutes at full speed. The supernatant was transferred to a fresh tube which was filled with EtOH (room temp.) followed by thorough but gentle mixing and spinning for 30 seconds. The pellet was washed with cold 70% EtOH, spun for 30 seconds and dried at room temperature. The pellet was resuspended in 50 μl TE (Tris-EDTA) and spun for 15 minutes. The supernatant was transferred to a fresh tube. 2.5 μl 10 mg/ml RNase was added, followed by incubation at 37° C. for 30 minutes and addition of 500 μl isopropanol with gentle mixing. The mixture was spun for 30 seconds, and the supernatant was removed. The pellet was rinsed with cold 96% EtOH and dried at room temperature. The DNA was dissolved in 50 μl water to a final concentration of approximately 100 μl/ml.

The DNA was transformed into *E. coli* by standard procedures. Two *E. coli* colonies were isolated and analysed with the restriction enzymes HindIII and XbaI which excised the DNA insert.

Some partial DNA sequences of the positive clone were determined, vide claim 4. The clone was found to encode a protein with an N-terminal amino acid sequence identical to the N-terminal on the purified β-galactanase.

EXAMPLE 3

Expression of galactanase

In order to express the galactanase, it was decided to introduce a heterologous signal sequence (in principle the sequence known from patent publication no. WO 91/17243) together with a DNA context 5' to the translation initiation codon, which should result in high level of translation initiation. The signal peptide was introduced by use of a PCR approach.

Construction of gene

The following two primers were used:

Primer 1, signal peptide (SEQ ID NO: 9)

HindIII
25 TAGCGAAGCTTCACA ATG CGT TCC TCC CCC CTC CTC CCG TCC GCC GTT GTG GCC GCC CTG
                         Met Arg Ser Ser Pro Leu Leu Pro Ser Ala Val Val Ala Ala Leu CCG GTG TTG GCC CTT GCA ! GCG CTC ACC TAT CGC GGC 3'
Pro Val Leu Ala Leu Ala ! Ala Leu Thr Tyr Arg Gly The underlined sequence is homologous to the 5' end of the gene, and ! indicate the processing site of the signal peptide.

Primer 2, 3' end
    5'GGGCGTGAATGTAAGCGTGAC3'

The PCR reaction was carried out by means of the Gene Amp kit and apparatus from Perkin Elmer Cetus, Norwalk, Conn., USA in accordance with the manufacturer's instructions.

The conditions were:

500 ng primer (the original cDNA clone)

100 p mol primer 1

100 p mol primer 2

10 µl 10 PCR buffer

10 µl 2 mM dNTP $H_2O$ ad 100 µl 2.5 U TAQ polymerase 30 cycles were run at 94° C. for 1 minute, 37° C. for 2 minutes, 72° C. for 2 minutes.

Figure 12:
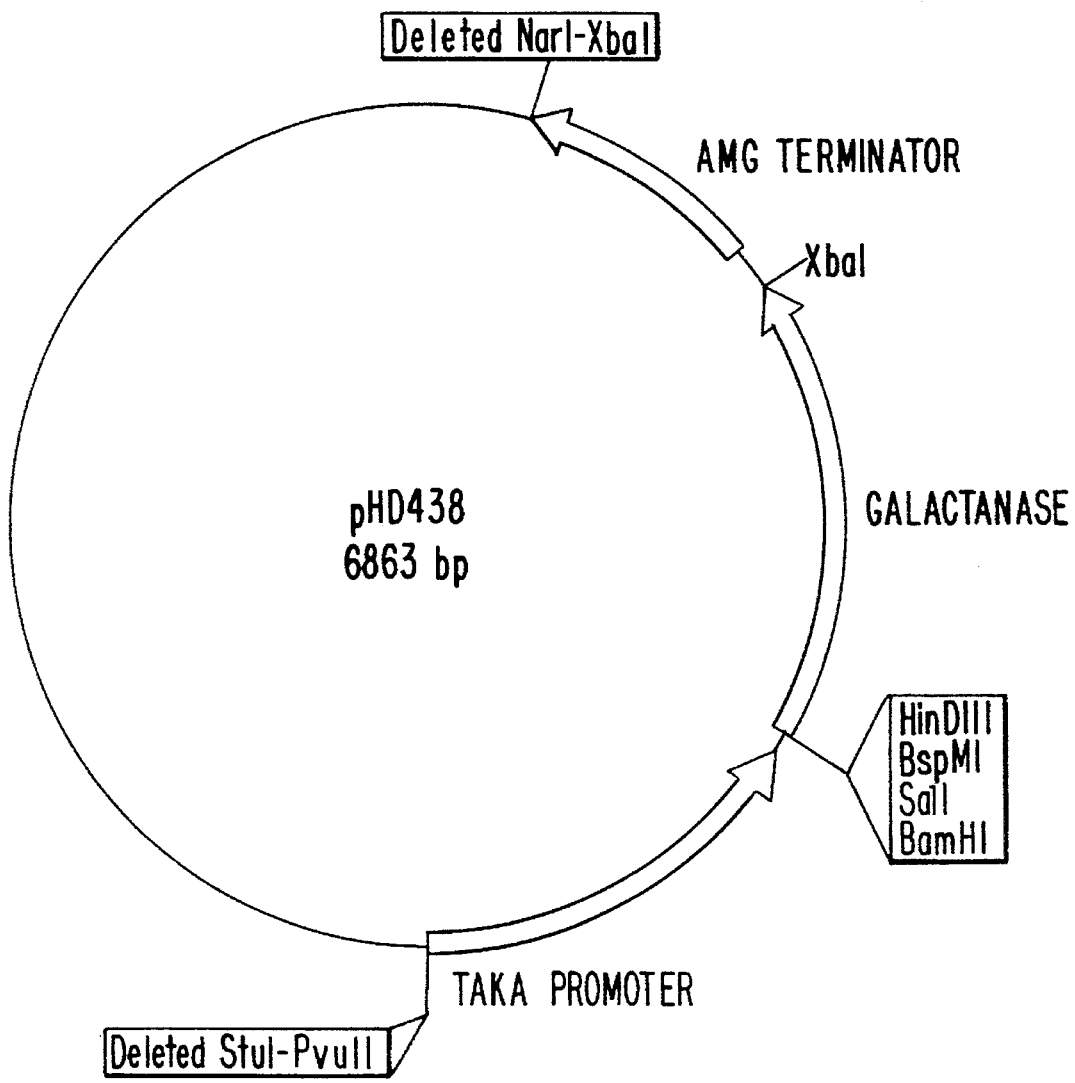
FIG. 12 shows a map of plasmid pHD438.

An aliquot of the reaction was analyzed on a 1% agarose gel. A band with the expected size was observed (approx. 1350 bp). The DNA was phenole extracted, ethanol precipitated and digested with the restriction enzymes HindIII/XbaI. The DNA was size fractionated on gel, and a fragment corresponding to the galactanase gene was purified. The gene was subsequently ligated to HindIII/XbaI digested pHD414 resulting in the plasmid pHD438, vide FIG. 12.

After amplification of the DNA in *E. coli* the plasmid pHD438 was transformed into *Aspergillus oryzae* as described above.

Test of *Aspergillus oryzae* transformants

Each of 18 transformants were inoculated in the center of a Petri dish with FG-4 agar. After 5 days of incubation at 30° C. 4 mm diameter plugs were removed from the center of the colonies by a cork borer. The plugs were imbedded in galactan overlayer gel, and incubated overnight at 40° C. The galactanase activity was visualized by Congo Red as described above. Some of the transformants had clearing zones at 30 mm and thereby demonstrates higher galactanase activity than the *Aspergillus oryzae* background which generated clearing zones of 14 mm. This demonstrates efficient expression of β-1,4-galactanase in *Aspergillus oryzae*. The 8 transformants with the highest galactanase activity were selected and inoculated and maintained on YPG-agar.

Each of the 8 selected transformants were inoculated from YPG-agar slants on 500 ml shake flask with FG-4 and MDU-2 media. After 4 days of fermentation with sufficient agitation to ensure good aeration, the culture broths were centrifuged for 10 minutes at 2000 g and the supernatants were analyzed.

A volume of 15 µl of each supernatant was applied to 4 mm diameter holes punched out in a galactanase overlayer gel (25 ml in a 13 cm diameter Petri dish). The galactanase activity was visualized by Congo Red after 20 hours of incubation.

In SDS-polyacrylamide gel electrophoresis (Pharmacia Excel-gel gradient 8–18) the *Aspergillus aculeatus* galactanase was identified by a western blot against antiserum raised against purified galactanase from *Aspergillus aculeatus*.

Uses of the β-1,4-galactanase according to the invention

The β-1,4-galactanase according to the invention can be used as a plant cell wall degrading enzyme, thus including the applications shown on page 35 of GB 2115820A.

If the β-1,4-galactanase according to the invention is used together with any pectinase preparation a synergistic effect or boosting effect can be demonstrated, especially in regard to TLP (total liquefaction power) on apple mash. If the pectinase preparation is the A.a.e.p., which is a pectinase preparation with special properties, vide GB 2115820A, a remarkable high synergistic effect or boosting effect can be demonstrated, especially in regard to TLP on apple mash.

TLP is the total liquefaction activity of an enzyme preparation. This activity is the total effect of all the single activities in this enzyme preparation. The reaction is followed rheologically. The decrease of the total viscosity (=a function of serum+structural viscosity) in a finely milled apple mash is monitored continuously within 2 hours with a rotary viscosimeter.

The enzymes are compared on a MOU-equal basis (Most Units), where per definition the TLP of Pectinex AP-18=0, and the TLP of Pectinex Ultra SP-L=100

A more detailed description of the MOU unit is to be found in the brochure "Determination of the pectinase units on apple juice (MOU)", which can be obtained on request from Novo Nordisk Ferment (Schweiz) AG, Neumatt, CH-4243 Dittingen, Switzerland.

Table 3 shows the TLP figures obtained by the galactanase alone and in combination with the A.a.e.p.

Figure 13:
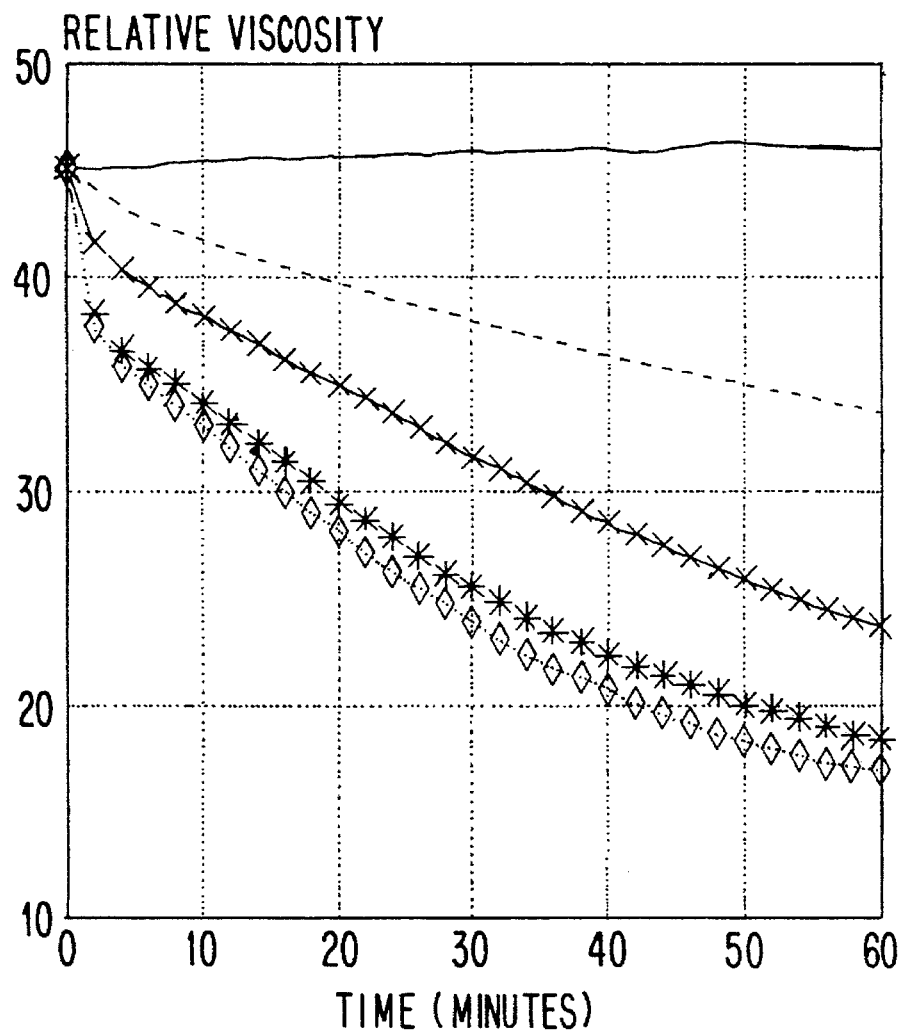
FIG. 13 graphically illustrates the viscosity of a β-1,4-galactanase alone and of the β-1,4-galactanase with a crude *Aspergillus aculeatus* preparation as a function of time.

Also, reference is made to FIG. 13. Both Table 3 and FIG. 13 show the marked synergism of the β-1,4-galactanase and the A.a.e.p. Thus, galactanase alone shows at higher dosages no effect at all on the viscosity. In lower dosages even an increase in viscosity can be observed. But surprisingly, in combination with the A.a.e.p. a very significant synergistic effect can be observed. An increase of about 30% (260%) of the galactanase units alone in the A.a.e.p. results in a TLP-increase of 60% (100%). This proves, that the µ-1,4-galactanase is a key activity for the liquefaction process of plant cell walls.

TABLE 3

| | Total liquefaction power (TLP) β-1,4-galactanase produced from A.a.e.p. | | | | | | |
|---|---|---|---|---|---|---|---|
| | Galactanase units | MOU/100 g mash | Protein:mg/ml Biorad | % protein added to A.a.e.p. protein Biorad | TLP expected % | TLP obtained % | TLP increase % |
| A.a.e.p. | 4.2 | 20 | 0.791 + 0 | 0 | 89 | 89 | 0 |
| A.a.e.p. + 1 part of gal. | 4.2 + 1.1 | 20 + 0.015 | 0.791 + 0.015 | 1.9 | 89 | 142 | 60 |
| A.a.e.p. + 10 parts of gal. | 4.2 + 11 | 20 + 0.15 | 0.791 + 0.15 | 19 | 89 | 181 | 103 |
| 10 parts of gal. | 11 | 0.15 | 0.15 | — | ? | (−25) | — |

Pectin extraction

Pectins have gelation and stabilisation properties, which make them useful for the food industry. They are commercially extracted from waste materials of the food industry, e.g. citrus peels, apple pomace or sugar-beet pulp.

Most often the extraction with acids (sulphuric acid or nitric acid) is used for the production of pectins. At a pH around 2 and at an elevated temperature the pectins are extracted from plant material and precipitated with alcohol after precipitation.

This acid extraction has several disadvantages: water pollution, corrosion, filtering problems due to desintegration of the plant cell walls, partial break down of the wanted pectin polymers (the degree of polymerisation is one of the most important parameters of a commercial pectin). Thus, it is obvious, that an extraction of pectins with enzymes, which do not decompose native pectin polymers would be of great advantage.

Industrial apple pomace for the pectin production was used to compare the amount of pectin extractable either by chemicals or β-1,4-galactanase.

Chemical extraction of pectin (prior art)

To 1 part of pomace 19 parts of distilled water was added and the mixture was heated to the boiling point in order to being the soluble part of the pomace into solution. The pH value was adjusted to 1.9 by means of 2N $H_2SO_4$. The mixture is held at this pH for 2.5 hours at 90° C. and afterwards cooled to room temperature. The mixture is filtered and the pomace residues washed with 10 parts of distilled water.

To 1 part of the filtrate 6 parts of methanol is added. After 30 minutes standing the mixture is filtered and pressed. The alcohol insoluble substance (AIS) is washed with 4 parts of methanol and filtered and pressed again.

The obtained AIS is dried at 60° C. for one hours.

From this AIS the amount of starch is determined with the test kit from Boehringer Mannheim (order no. 207748).

The amount of obtained pectin is calculated by determination of the amount of AIS in % obtained from the dry matter substance from the pomace and subtracting the amount of starch in the AIS.

Enzymatic extraction of pectin

To 1 part of pomace 19 parts of 0.1 m sodium acetate buffer of pH 5.0 (with 0.02% $NaN_3$) is added. At 30° C. the mixture is treated for 20 hours with solutions of the purified μ-1,4-galactanase according to the invention. Afterwards the mixture is filtered and the pomace residues washed with 10 parts of distilled water.

The AIS is obtained in the way described above.

Results

With the chemical extraction 17.5% pectin was obtained whereas with the enzymatic extraction between 11 and 14.5% were obtained, depending upon the amount of β-1,4-galactanase used.

These results prove, that the β-1,4-galactanase is one of the key enzymes for enzymatic extraction of pectins from plant material. Also, it appears from the above that 60 to 80% of the pectin extractable by chemical means and with all the accompanying disadvantages can be extracted enzymatically in an environmental sound manner.

---

We claim:

1. An isolated β-1,4-galactanase obtainable from *Aspergillus aculeatus* which has
    (a) a pH-optimum between 3.0 and 5.0,
    (b) an isoelectric point of 2.5–3.5,
    (c) a molecular weight of between 30,000 and 50,000, and
    (d) a temperature optimum between 10° and 50° C.

2. A β-1,4-galactanase according to claim 1, which has a pH-optimum between 3.5 and 4.0.

3. A β-1,4-galactanase according to claim 1, which has a temperature optimum between 25° and 40° C.

4. A β-1,4-galactanase according to claim 1, which has a pH-optimum between 3.5 and 4.0 and a temperature optimum between 25° and 40° C.

5. A β-1,4-galactanase according to claim 1, which is obtainable from *Aspergillus aculeatus*, CBS 101.43.

6. A β-1,4-galactanase according to claim 1 which has the following partial amino acid sequence (SEQ ID NO: 1)
Ala Leu Thr Tyr Arg Gly Ala Asp Ile Ser Ser
Leu Leu Leu Leu Glu Asp Glu Gly Tyr Ser
Tyr Lys Asn Leu Asn Gly Gln Thr Gln Ala.

7. An enzyme preparation comprising a pectinase preparation and a β-1,4-galactanase according to claim 1.

8. An enzyme preparation according to claim 7, wherein the pectinase preparation is obtainable from Aspergillus.

9. An enzyme preparation according to claim 8, wherein the pectinase preparation is obtainable from *Aspergillus niger, Aspergillus aculeatus, Aspergillus awamori* or *Aspergillus oryzae*.

10. A method of modifying a galactane, comprising adding a β-1,4-galactanase according to claim 1, to the galactane.

11. A method of modifying a cell wall of a plant, comprising adding a β-1,4-galactanase according to claim 1 to the plant cell wall.

\* \* \* \* \*